(12) United States Patent
Kahook et al.

(10) Patent No.: US 11,951,040 B2
(45) Date of Patent: *Apr. 9, 2024

(54) OPHTHALMIC DEVICE

(71) Applicant: NEW WORLD MEDICAL, INC., Rancho Cucamonga, CA (US)

(72) Inventors: Malik Y. Kahook, Denver, CO (US); Eric Porteous, Corona, CA (US); Carlos A. Mendoza, Irvine, CA (US)

(73) Assignee: NEW WORLD MEDICAL INC., Rancho Cucamonga, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/747,566

(22) Filed: May 18, 2022

(65) Prior Publication Data

US 2022/0273492 A1 Sep. 1, 2022

Related U.S. Application Data

(63) Continuation of application No. 17/381,950, filed on Jul. 21, 2021, now Pat. No. 11,364,146, which is a
(Continued)

(51) Int. Cl.
*A61F 9/007* (2006.01)
*A61M 5/145* (2006.01)
(Continued)

(52) U.S. Cl.
CPC ....... *A61F 9/00781* (2013.01); *A61M 5/3134* (2013.01); *A61M 5/3146* (2013.01);
(Continued)

(58) Field of Classification Search
CPC .............. A61F 9/00781; A61F 9/00736; A61F 9/0008; A61F 9/007; A61M 5/3146;
(Continued)

(56) References Cited

U.S. PATENT DOCUMENTS 2,156,023 A 4/1939 McKay
2,725,877 A 12/1955 Reiter
(Continued)

FOREIGN PATENT DOCUMENTS

CN 104105513 A 10/2014
CN 104540472 A 4/2015
(Continued)

OTHER PUBLICATIONS

Chinese Office Action for Application No. 201980085570.6, dated Feb. 11, 2023, 18 pages including translation.
(Continued)

*Primary Examiner* — Robert J Utama
*Assistant Examiner* — Leah J Swanson
(74) *Attorney, Agent, or Firm* — Morgan, Lewis & Bockius LLP

(57) ABSTRACT

An ophthalmic device including a cannula having a cannula distal end, a lumen, and one or more orifices coupled to the lumen is provided. The cannula is configured to deliver a fluid. A sleeve is disposed around the cannula and has a sleeve distal end. A handle is coupled to the sleeve and the cannula, the handle having an actuator. An internal mechanism is coupled to the actuator and is configured to pump the fluid. The internal mechanism includes an inlet port disposed on a handle proximal end, a drive member coupled to the actuator and a plunger coupled to the drive member. The ophthalmic device is configured to retain a volume of fluid and to be prevented from being re-primed after a predetermined number of actuator presses, wherein the retained volume of fluid is dispensed over an additional number of actuator pushes.

16 Claims, 24 Drawing Sheets

Related U.S. Application Data continuation of application No. 16/984,077, filed on Aug. 3, 2020, now Pat. No. 11,147,709, which is a continuation of application No. 16/707,213, filed on Dec. 9, 2019, now Pat. No. 10,729,584, which is a continuation of application No. PCT/US2019/056482, filed on Oct. 16, 2019.

(60) Provisional application No. 62/750,151, filed on Oct. 24, 2018.

(51) Int. Cl.
*A61M 5/31* (2006.01)
*A61M 5/315* (2006.01)
*A61M 5/46* (2006.01)

(52) U.S. Cl.
CPC ...... *A61M 5/3148* (2013.01); *A61M 5/31585* (2013.01); *A61M 5/46* (2013.01); *A61M 2005/14533* (2013.01); *A61M 2005/3103* (2013.01); *A61M 2005/312* (2013.01)

(58) Field of Classification Search
CPC ...... A61M 5/50; A61M 5/5013; A61M 5/502; A61M 2005/5026; A61M 2005/5033; A61M 2005/5046; A61M 2005/5053; A61M 5/5066; A61M 2005/5073; A61M 5/504; A61M 5/3134; A61M 5/3148; A61M 5/31585; A61M 5/46; A61M 5/145; A61M 5/14526; A61M 5/1454; A61M 5/16804; A61M 5/16809; A61M 5/31501; A61M 5/31526; A61M 5/3153; A61M 5/31535; A61M 5/31536; A61M 5/31538; A61M 5/31541; A61M 5/31596; A61M 5/31595; A61M 5/3156; A61M 5/31576; A61M 5/31578; A61M 5/3158; A61M 2005/3103; A61M 2005/312; A61M 2005/1402; A61M 2005/14506; A61M 2005/14533; A61M 2005/204; A61M 2005/3101; A61M 2005/3114; A61M 2005/3115; A61M 2005/3128; A61M 2005/3152; A61M 2210/0612; A61M 5/315; A61M 2025/0004; A61M 2025/0175; A61M 25/007

See application file for complete search history.

(56) References Cited

U.S. PATENT DOCUMENTS

| | | | |
|---|---|---|---|
| 4,685,910 | A | 8/1987 | Schweizer |
| 5,163,915 | A | 11/1992 | Holleron |
| 6,010,485 | A | 1/2000 | Buch-Rasmussen et al. |
| 10,213,555 | B1 | 2/2019 | Carranza et al. |
| 10,729,584 | B2 * | 8/2020 | Kahook .................. A61M 5/46 |
| 11,147,709 | B2 * | 10/2021 | Kahook .............. A61F 9/00781 |
| 11,364,146 | B2 * | 6/2022 | Kahook .................. A61M 5/46 |
| 2001/0008961 | A1 | 7/2001 | Hecker et al. |
| 2001/0037087 | A1 * | 11/2001 | Knauer .................. A61M 5/204 604/137 |
| 2006/0276753 | A1 | 12/2006 | Kronestedt et al. |
| 2007/0073275 | A1 | 3/2007 | Conston et al. |
| 2007/0191925 | A1 | 8/2007 | Dorn |
| 2008/0082078 | A1 | 4/2008 | Berlin |
| 2008/0221530 | A1 | 9/2008 | Glejbol et al. |
| 2010/0211079 | A1 | 8/2010 | Aramant |
| 2012/0123434 | A1 | 5/2012 | Grabner et al. |
| 2012/0165734 | A1 | 6/2012 | Auld et al. |
| 2012/0310111 | A1 | 12/2012 | Shachar et al. |
| 2013/0197592 | A1 | 8/2013 | Mafi |
| 2013/0253402 | A1 | 9/2013 | Badawi et al. |
| 2013/0253528 | A1 | 9/2013 | Haffner et al. |
| 2013/0267931 | A1 | 10/2013 | Nazzaro et al. |
| 2013/0281908 | A1 | 10/2013 | Schaller et al. |
| 2013/0297011 | A1 | 11/2013 | Morris et al. |
| 2014/0039456 | A1 | 2/2014 | Lerner |
| 2014/0236098 | A1 | 8/2014 | Mica et al. |
| 2014/0257241 | A1 | 9/2014 | Sutkin et al. |
| 2015/0065940 | A1 | 3/2015 | Rangel-Friedman et al. |
| 2015/0133946 | A1 | 5/2015 | Horvath et al. |
| 2016/0074211 | A1 | 3/2016 | Ko et al. |
| 2016/0151204 | A1 | 6/2016 | Haffner et al. |
| 2016/0287438 | A1 | 10/2016 | Badawi et al. |
| 2016/0325050 | A1 | 11/2016 | Gonçalves |
| 2017/0216092 | A1 | 8/2017 | Singh |
| 2017/0296753 | A1 | 10/2017 | Rowe et al. |
| 2018/0028358 | A1 | 2/2018 | Andino et al. |
| 2018/0168863 | A1 | 6/2018 | Kahook |
| 2018/0339110 | A1 | 11/2018 | Stiffler |
| 2019/0105077 | A1 | 4/2019 | Kalina, Jr. et al. |
| 2019/0274825 | A1 | 9/2019 | Kanner et al. |

FOREIGN PATENT DOCUMENTS

| | | | | |
|---|---|---|---|---|
| CN | 106029019 | A | 10/2016 | |
| EP | 3064241 | A1 | 9/2016 | |
| JP | 2011050791 | A | 3/2011 | |
| JP | 2013508096 | A | 3/2013 | |
| JP | 2015515887 | A | 6/2015 | |
| JP | 2015517836 | A | 6/2015 | |
| JP | 2016520383 | A | 7/2016 | |
| JP | 2016526991 | A | 9/2016 | |
| JP | 2018512963 | A | 5/2018 | |
| JP | 2018513696 | A | 5/2018 | |
| WO | WO-0051668 | A1 | 9/2000 | |
| WO | WO-2016159999 | A1 | 10/2016 | |
| WO | WO-2016186965 | A2 * | 11/2016 | ............. A61M 5/24 |
| WO | WO-2017180480 | A1 | 10/2017 | |
| WO | WO-2018118817 | A1 | 6/2018 | |

OTHER PUBLICATIONS

Extended European Search Report for Application No. 19875683.5, dated Jul. 22, 2022, 9 pages.
Extended European Search Report for Application No. 19876723.8, dated Jun. 14, 2022, 9 pages.
International Search Report and Written Opinion for Application No. PCT/US2019/56480, dated Mar. 4, 2020, 23 pages.
International Search Report and Written Opinion for Application No. PCT/US2019/56482, dated Feb. 7, 2020, 12 pages.
Invitation to Pay Additional Fees for Application No. PCT/US2019/56480, dated Dec. 13, 2019, 2 pages.
Invitation to Pay Additional Fees for Application No. PCT/US2019/56482, dated Dec. 13, 2019, 2 pages.
Japanese Office Action for Application No. 2021-522439, dated Oct. 31, 2023, 11 pages including translation.
Japanese Office Action for Application No. 2021-522515, dated Sep. 26, 2023, 8 pages including translation.

* cited by examiner

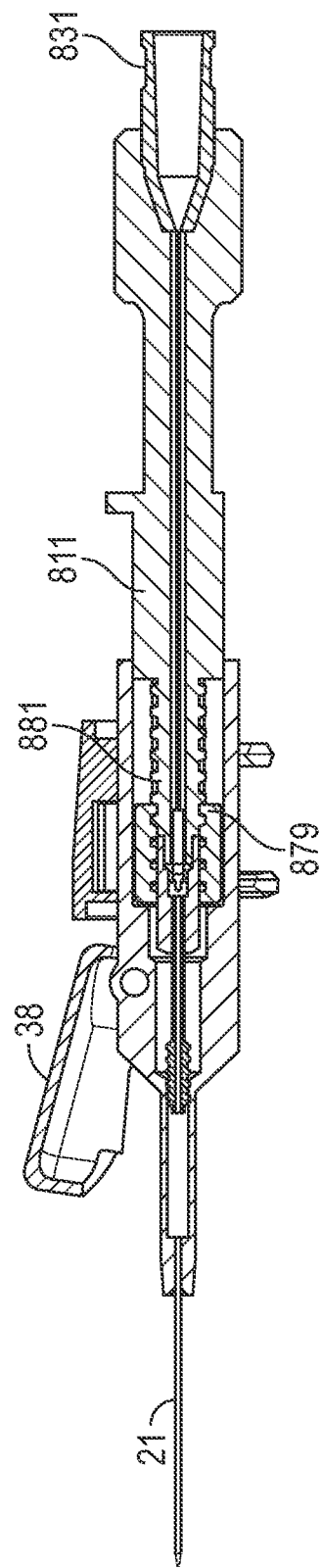

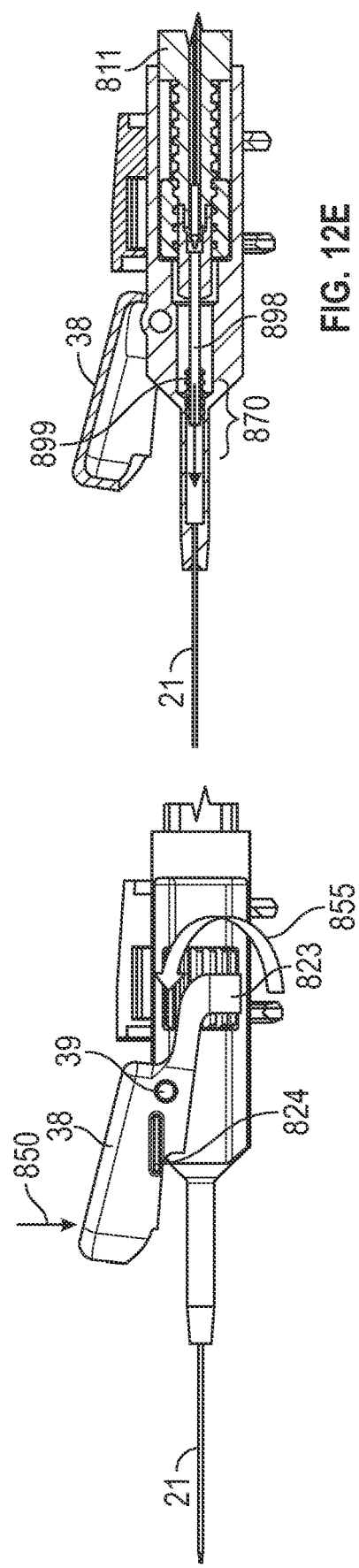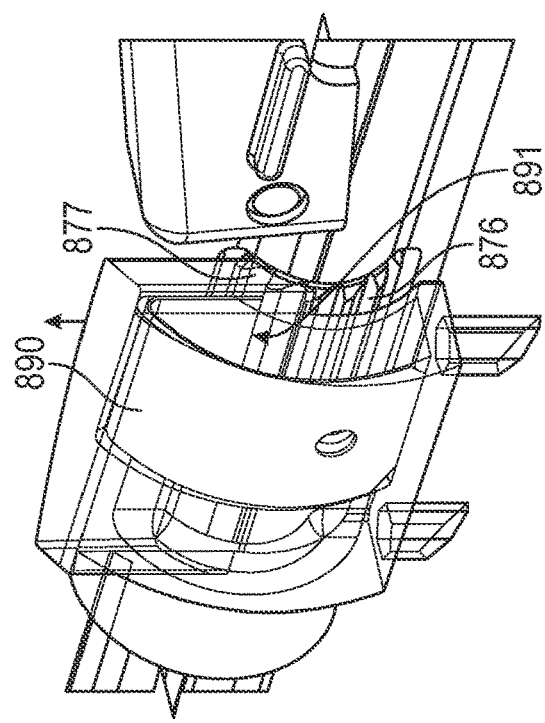

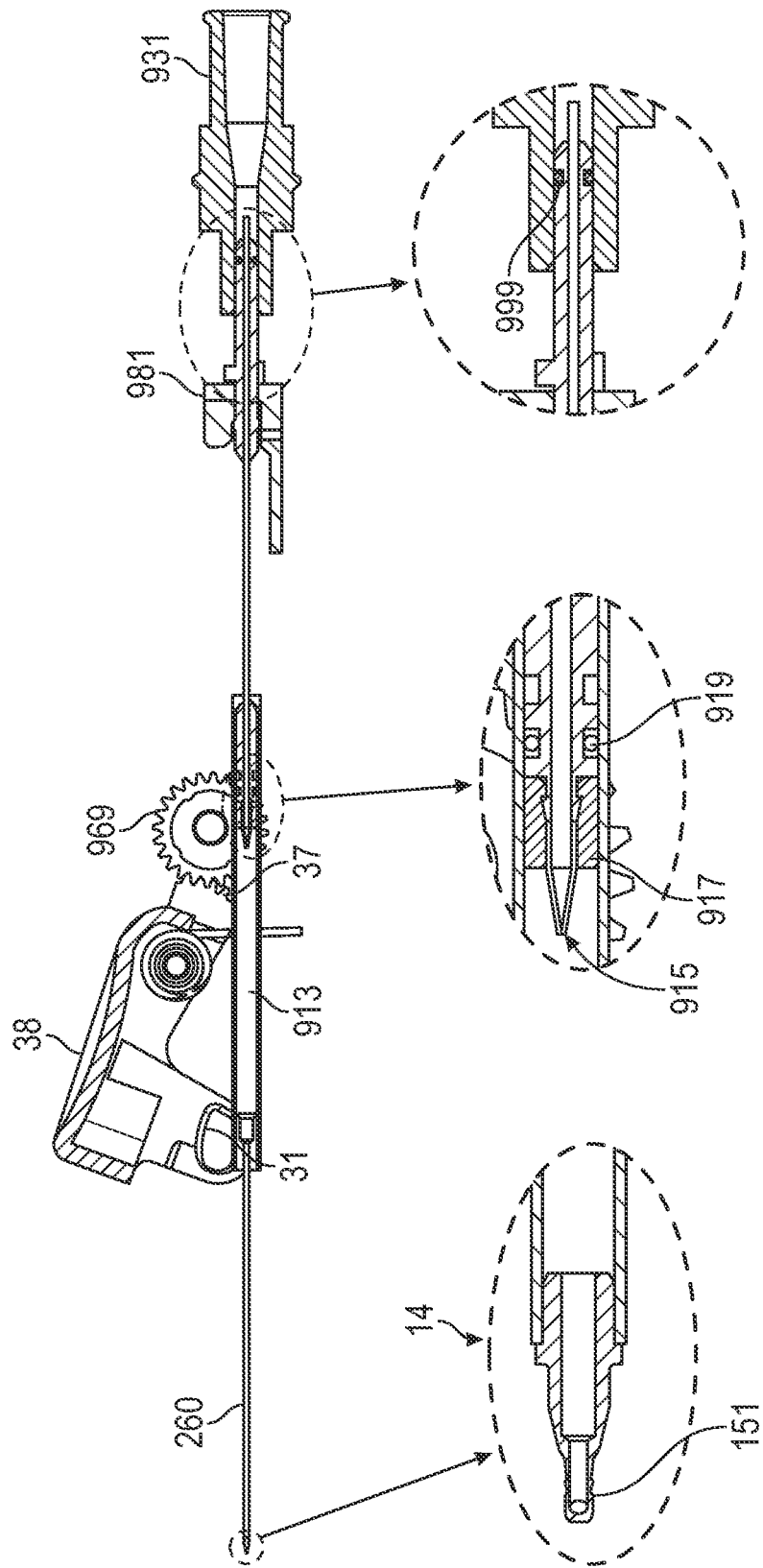

OPHTHALMIC DEVICE

CROSS-REFERENCE TO RELATED APPLICATIONS

This application is a continuation of U.S. patent application Ser. No. 17/381,950, filed on Jul. 21, 2021, entitled "OPHTHALMIC DEVICE," which issued as U.S. Pat. No. 11,364,146 on Jun. 21, 2022, which is a continuation of U.S. patent application Ser. No. 16/984,077, filed on Aug. 3, 2020, entitled "OPHTHALMIC DEVICE," which issued as U.S. Pat. No. 11,147,709 on Oct. 19, 2021, which is a continuation of U.S. patent application Ser. No. 16/707,213, filed on Dec. 9, 2019, entitled "OPHTHALMIC DEVICE," which issued as U.S. Pat. No. 10,729,584 on Aug. 4, 2020, which is a continuation of and claims priority to International Patent Application No. PCT/US2019/056482, filed Oct. 16, 2019, which claims the benefit of priority under 35 U.S.C. § 119 from U.S. Provisional Application No. 62/750, 151, entitled "OPHTHALMIC DEVICE," filed Oct. 24, 2018, the entirety of which are incorporated herein by reference.

TECHNICAL FIELD

The present disclosure generally relates to medical devices and procedures, and more particularly, to an ophthalmic device.

BACKGROUND

Glaucoma is a disease resulting from an increase in intraocular eye pressure (IOP). IOP may increase when natural drainage of the eye (e.g., drainage of the humus of the eye) is prevented, reduced, or otherwise blocked. Cavities in front of (e.g., on top of) the lens of the eye are filled with a viscous fluid called aqueous humor. A continuous flow of aqueous humor through the eye provides nutrition to portions of the eye (e.g., the cornea and the lens) that have no blood vessels. This flow of aqueous humor also removes waste (e.g., foreign object debris) from these tissues. In a healthy eye, a stream of aqueous humor drains out of the anterior chamber of the eye through the trabecular meshwork and into Schlemm's canal as new aqueous humor is secreted by the epithelial cells of the ciliary body. The drained aqueous humor enters the venous blood stream from Schlemm's canal and is carried along with the venous blood leaving the eye. When the natural drainage mechanisms of the eye (e.g., Schlemm's canal and/or the trabecular meshwork) stop functioning properly, the IOP begins to increase.

BRIEF DESCRIPTION OF THE DRAWINGS

The accompanying drawings, which are incorporated in and constitute a part of this specification, illustrate exemplary aspects of the present disclosure and together with the description, serve to explain the principles of the disclosure.

FIG. 2A shows the inner cannula covered by the sleeve and FIG. 2B shows inner cannula protruding from the sleeve.

FIG. 3A shows the sleeve in a distal position and FIG. 3B shows the sleeve in a retracted proximal position.

FIG. 4A shows an example of a sleeve sized to abut against a trabecular meshwork over a Schlemm's canal and a more rigid anatomy neighboring the Schlemm's canal. FIG. 4B shows an example of a sleeve sized to collapse the trabecular meshwork into the Schlemm's canal.

FIG. 5A is a perspective view of the sleeve, FIG. 5B is a top view of the sleeve, and FIG. 5C is a side view of the sleeve.

FIG. 6A is a perspective view of the sleeve, FIG. 6B is a top view of the sleeve, and FIG. 6C is a side view of the sleeve.

FIG. 7A is a perspective view of cannula, FIG. 7B is a top view of the cannula as implemented in FIG. 7A, and FIG. 7C is a side view of cannula as implemented in FIG. 7A.

FIG. 9A shows the mechanism in a starting position, FIG. 9B shows the mechanism in an intermediate position, and FIG. 9C shows the mechanism in a released position.

FIG. 11A shows a nut and a pump of the mechanism with a linkage removed, FIG. 11B shows a linkage in an initial position, and FIG. 11C shows the linkage in an actuated position.

FIGS. 12B-12C are perspective and sectional views of internal components of the ophthalmic device of FIG. 12A.

FIGS. 12D-12F are various portion views of the internal components of the ophthalmic device of FIG. 12A, illustrating component action during actuation.

FIGS. 13B-13C are perspective and sectional views of internal components of the ophthalmic device of FIG. 13A.

FIG. 15A shows the ophthalmic device entering an anterior chamber and FIG. 15B shows the ophthalmic device injecting a fluid into a Schlemm's canal.

DETAILED DESCRIPTION

Figure 1:
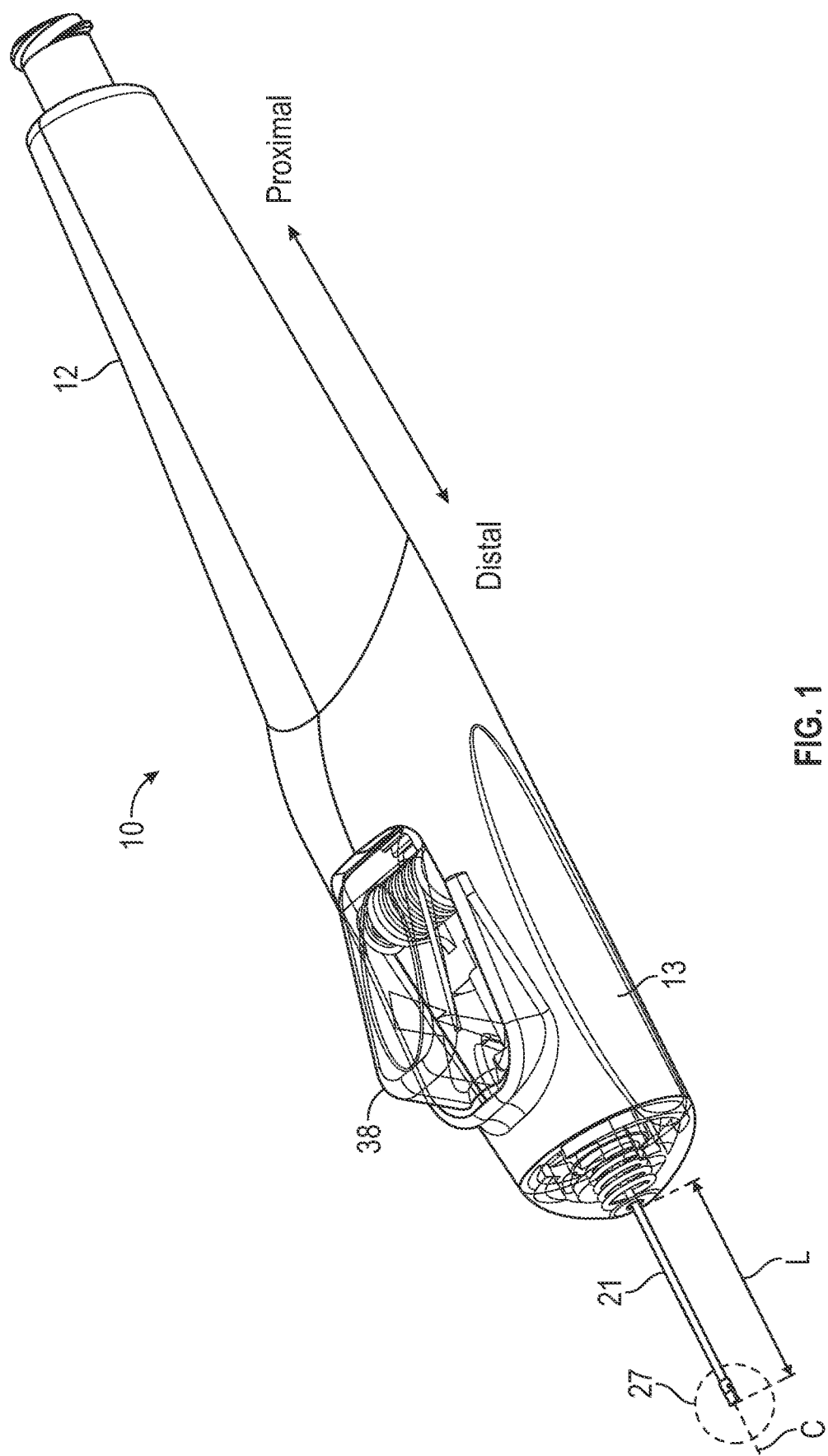
FIG. 1 is a perspective view showing an example of an ophthalmic device.

The following detailed description is exemplary and explanatory only and is not restrictive of the features, as claimed. As used herein, the terms "comprises," "comprising," or other variations thereof, are intended to cover a non-exclusive inclusion such that a process, method, article, or apparatus that comprises a list of elements does not include only those elements, but may include other elements not expressly listed or inherent to such a process, method, article, or apparatus. Additionally, the term "exemplary" is used herein in the sense of "example," rather than "ideal." As used herein, the terms "about," "substantially," and "approximately," indicate a range of values within +/−5% of a stated value. The term "distal" refers to a portion farthest away from a user when introducing a device into a subject. By contrast, the term "proximal" refers to a portion closest to the user when placing the device into the subject.

Embodiments discussed below relate to a medical device, such as an ophthalmic device configured for use in the treatment of glaucoma or other eye conditions, and related methods of use. According to some embodiments, the ophthalmic device can have a distal end including a cannula. The cannula can include an inner lumen and one or more outflow orifices configured for delivery of viscoelastic fluid or other substance into a target site of a patient, such as a Schlemm's canal.

According to some embodiments, a tip of the cannula can include a collar disposed around an outer surface of the cannula. The collar can be configured to interact with intraocular tissue in an aqueous outflow pathway of a patient's eye to facilitate positioning of the cannula or facilitate fluid transfer with respect to the eye. For example, the collar can include a radially protruding lip that is fixed or movable to a position proximal to the orifices to provide a structure that facilitates positioning of the orifices of the cannula within or near Schlemm's canal.

According to some embodiments, the collar can be implemented as part of a retractable sleeve. The sleeve can be disposed around the cannula and configured to retract relative to the cannula to pull patient tissue via a suction effect. For example, manipulation of a button or other actuator component disposed on a handle of the device can be configured to retract the sleeve to pull a trabecular meshwork over and around the cannula to penetrate the meshwork with the cannula and open up the canal to facilitate fluid delivery therein.

According to some embodiments, a mechanism can be configured to retract the sleeve or otherwise move a component of the ophthalmic device with a relatively quick and sharp snapping motion. Such a motion can, for example, facilitate suction of the patient's tissue and penetration thereof by the cannula. Additionally or alternatively, the mechanism can operate a pump to inject the fluid or substance through the cannula in concert with the retraction of the sleeve.

These and other embodiments are discussed below in relation to particular examples illustrated in FIGS. 1-9B. However, various modifications and alternative applications will be appreciated by those skilled in the art. Thus, the detailed description provided with respect to these figures as well as the description provided above should not be construed as limiting but rather serves to explain various concepts associated with this disclosure.

FIG. 1 shows an example of a medical device, and more particularly, shows an example of an ophthalmic device 10. In the example shown, the ophthalmic device 10 is configured as a medical instrument or minimally invasive surgical instrument configured to interact with ocular tissue to facilitate injection of a substance into a Schlemm's canal or other intraocular site of an eye of a patient. However, while examples herein are described with reference to ophthalmic instruments and procedures, it will be appreciated that teachings of the ophthalmic device 10 can be readily applied to or adapted for any of a variety of other medical and non-medical applications. These can include, for example, other medical procedures involving interactions with patient tissue other than in the patient's eye, and other non-medical applications involving fluid injection or transfer.

Referring to FIG. 1, the ophthalmic device 10 can include a handle 12 coupled to an ocular component 21. The ocular component 21 is generally configured for interacting with ocular tissue and/or insertion into an intraocular cavity, such as the anterior chamber of an eye of a patient. The ocular component 21 can be configured to facilitate fluid delivery, tissue manipulation, and/or other interactions with the eye of the patient.

As shown in the example of FIG. 1, the ocular component 21 can include an elongated tubular member protruding from a distal end of the handle 12 and defining a central longitudinal axis C. The ocular component 21 can have a working length L and a diameter that permits insertion into the anterior chamber through a corneal incision or other incision on an eye of a patient. The working length L described herein can be defined as the exposed length or distance of the ocular component 21 protruding from the handle 12, extending from the distal end of the handle 12 to the distal end of the ocular component 21. The working length L can be, for example, in the range of between about 16 millimeters (mm) and 40 mm, or more particularly about 18 mm, although it contemplated that other dimensions outside of these examples may be suitable in various implementations. The diameter may vary across the working length L or be constant throughout the working length L and can be, for example, in the range of about 100 micrometers ($\mu$m) to 1000 $\mu$m, or more particularly about 700 $\mu$m, although it is contemplated that other dimensions outside of these example may be suitable in various implementations. As shown in the example of FIG. 1, the ocular component 21 can be implemented with a straight geometry (defining a straight central axis C), or the ocular component 21 can be implemented with a curved and/or bent geometry.

With continued reference to FIG. 1, the handle 12 can be implemented as a main body of the ophthalmic device 10 and can be configured to be manipulated by the hand of a user or other operator. For example as shown in FIG. 1, the handle 12 can be implemented as an elongated tubular member having a distal end and a proximal end opposite to the distal end. This can, for example, facilitate gripping or manipulation of the handle 12 using a pencil-grip by a surgeon, although it is contemplated that handle 12 can be implemented with other shapes and configurations, such as pistol-shaped arrangements and/or finger loops. An outer surface of the handle 12 can include finger grips 13 having a contoured shape and/or textured surface (e.g., knurled, ribbed, or other surface textures) to facilitate grasping of the handle 12 by the user. Implementations are also contemplated in which the outer surface of the handle 12 has a straight non-contoured shape and/or a smooth outer surface.

The handle 12 can include or be coupled to an actuator 38. The actuator 38 can be coupled to one or more moving parts of the ophthalmic device 10 to provide one or more operative functions that facilitate performance of an ophthalmic procedure using the device. For example, the actuator 38 can be configured to move one or more parts of the ocular component 21 independently of the handle 12 and/or move two or more moving parts of the ocular component 21 independently of each other. Additionally or alternatively, the actuator 38 can be configured to actuate a pump, plunger, and/or squeeze mechanism for fluid transfer through the ocular component 21. The actuator 38 can, for example, be configured to move the part(s) directly or via an internal mechanism disposed in the handle 12.

In the example shown in FIG. 1, the actuator 38 is implemented as or otherwise includes a mechanical push button disposed on the handle 12 and movable between an un-pressed and pressed position. The push button is shown disposed on a lateral side of the handle 12 which can, for example, facilitate actuation by a surgeon or other user using their thumb and/or index finger when the handle 12 is grasped in the hand of the user during a procedure. Additionally or alternatively, implementations are contemplated in which the push button is disposed in other locations, such as a proximal end of the handle, for example. Implementations are also contemplated in which, instead of or in addition to the push button, the actuator 38 includes a slider, roller wheel, squeeze bulb, and/or any other suitable mechanism that can be manipulated by a user or other operator to actuate a moving part of the ophthalmic device 10.

Figure 2A:
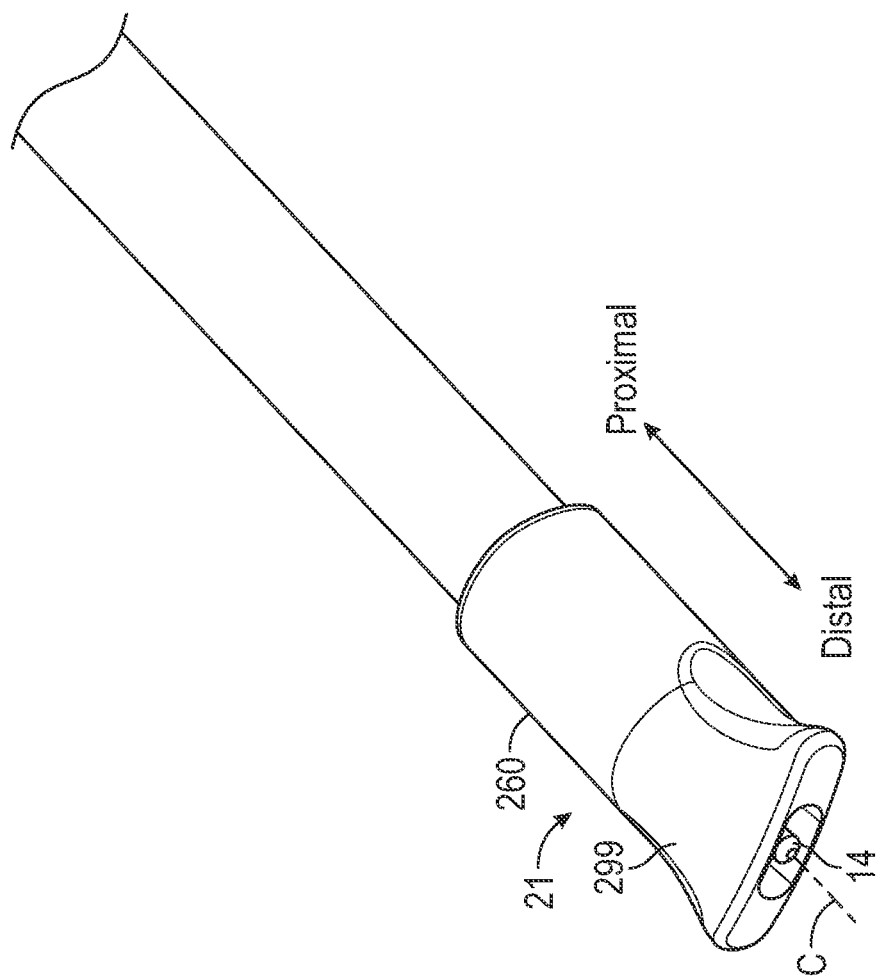
FIGS. 2A-2B are perspective views showing a distal end of an example of an ophthalmic device that has an inner cannula surrounded by a sleeve.
Figure 2B:
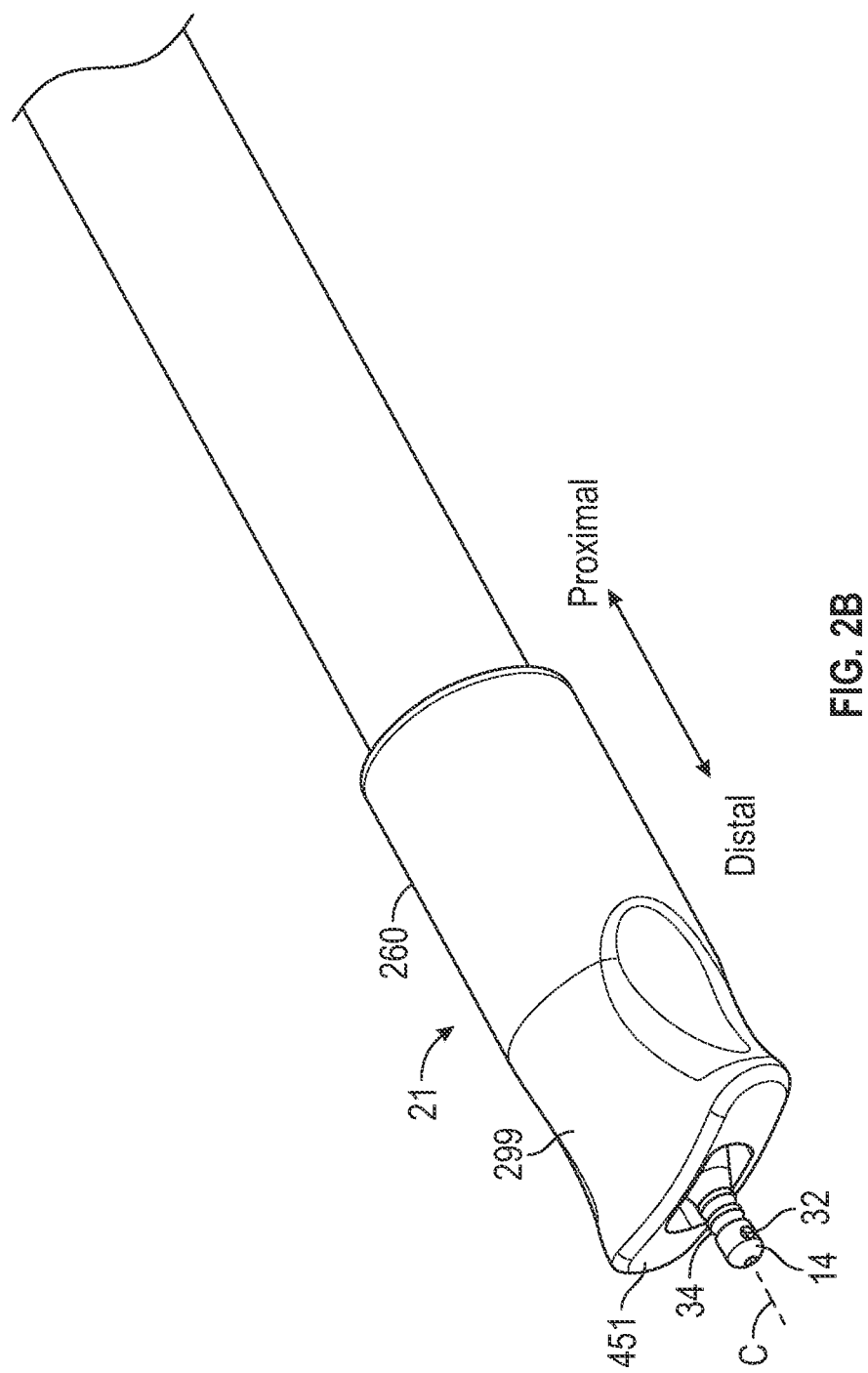

FIGS. 2A and 2B are enlarged views showing an example of an ocular component 21 that can be included in the ophthalmic device 10. FIGS. 2A and 2B show a distal portion 27 of the ocular component 21 as indicated in FIG. 1.

In the example shown in FIGS. 2A and 2B, the ocular component 21 includes a cannula 14 and a sleeve 260 (also sometimes referred to herein as a "sheath"). The sleeve 260 is disposed around the cannula 14 and the cannula 14 is disposed within the sleeve 260. The cannula 14 and the sleeve 260 can, for example, each be implemented as substantially tubular components in which the cannula 14 is disposed coaxially with the sleeve 260 and both the cannula 14 and the sleeve 260 are disposed about the central axis C. The cannula 14 and/or sleeve 260 can, for example, each have a working length equivalent to the working length L of the ocular component 21.

The cannula 14 and the sleeve 260 can be configured for relative movement with respect to each other. For example as shown in FIGS. 2A and 2B, the cannula 14 and the sleeve 260 can be moveable with respect to each other between a first configuration (shown in FIG. 2A) in which the distal end of the cannula 14 is substantially covered or encased by the sleeve 260, and a second configuration (shown in FIG. 2B) in which the distal end of the cannula 14 protrudes distally from the distal end of the sleeve 260. The relative movement can be accomplished by, for example, retraction of the sleeve 260 in a proximal direction independently of the cannula 14 and the handle 12, and/or by deployment of the cannula 14 in a distal direction independently of the sleeve 260 and the handle 12. The actuator 38 can be operatively coupled to the cannula 14 and/or sleeve 260 to move the cannula 14 and/or sleeve 260 with respect to a fixed component of the handle 12.

The cannula 14 can be configured to transfer a fluid or other substance. For example, the cannula 14 can be configured for injection of a viscoelastic fluid, such as sodium hyaluronate or chondroitin sulfate. Viscoelastic fluid is a highly pliable, gel-like material which helps provide enough space for adequate drainage and eye pressure relief by expanding tissue structures away from one another, to re-open or expand a flow path of aqueous humor. Viscoelastic fluid also may clear an obstructed view by expanding bleeding structures away from one another to improve visualization. It is also contemplated that the cannula 14 can be utilized to deliver stem cells, medicaments, gases (e.g., SF6 or C3F8), and/or dyes (e.g., trypan blue dye). Injected stem cells, for example, can initiate growth of healthy tissues within the eye (e.g., to develop healthy trabecular meshwork to enhance drainage of aqueous humor there through). Injected dye, for example, can flow through the trabecular meshwork to enhance visualization of aqueous humor fluid flow to determine which areas, if any, of the trabecular meshwork remain blocked, collapsed, or otherwise impede flow of aqueous humor. Further, while examples are described with respect to the injection of substances, it is contemplated that the cannula 14 can additionally or alternatively be utilized to withdraw substances, such as to withdraw tissue, blood, aqueous humor, or other substances out of a Schlemm's canal or other part of an eye.

As shown in FIG. 2B, the cannula 14 can be implemented as a blunt microcannula having a rounded, unsharpened, or otherwise atraumatic tip at its distal end. While implementations are also contemplated in which the cannula 14 is implemented with a sharp needle or traumatic tip at its distal end, the blunt cannula can facilitate penetration of porous patient tissue, such as a trabecular meshwork, while mitigating risk of undesired trauma to surrounding tissue.

The cannula 14 can include one or more orifices 32 disposed on a distal portion of the cannula 14, e.g., disposed on or near the cannula distal e0n0
. . . d. The one or more orifices 32 can provide one or more fluid transfer ports configured to transfer a fluid or other substance. For example, the one or more orifices 32 can be configured to provide outflow ports for delivery of a viscoelastic substance to a Schlemm's canal of an eye of a patient. As shown in the example of FIG. 2B, the one or more orifices 32 can be disposed on a lateral side of the cannula 14 which can provide one or more fluidic channels through a sidewall of the cannula 14 in a direction transverse to the central axis C. Alternatively, other implementations are contemplated in which the orifices are disposed along the central axis C and/or in any other one or more suitable positions to transfer fluid to and/or from an intended target site. The orifices can each have a diameter of between 30 µm to 70 µm, or such as about 50 µm or about 60 µm, although it is contemplated that other orifice diameters outside of these ranges may be suitably used in various implementations. The cannula 14 may include one or more grooves 34 disposed on a distal portion of the cannula 14.

As shown for example in FIGS. 2A and 2B, relative movement between the sleeve 260 and the cannula 14 can be configured to selectively cover and uncover one or more of the orifices 32 with the sleeve 260. For example, when in the first configuration shown in FIG. 2A, the distal end of the sleeve 260 can be disposed at a first axial position distal to the orifice(s) 32 so as to cover or surround the orifice(s) 32, and when in the second configuration shown in FIG. 2B, the distal end of the sleeve 260 can be disposed at a second axial position proximal to the orifice(s) 32 so as to expose the orifice(s) 32 outside of the distal end of the sleeve 260.

The ophthalmic device 10 can further include a collar 299 disposed about a circumference of a tip of the cannula 14 at or near the cannula distal end. For example as shown in FIGS. 2A and 2B, the collar 299 can be an integral part of the sleeve 260 or otherwise fixedly coupled to the sleeve 260 at the sleeve distal end, in which case collar 299 can move together with the sleeve 260 so that the collar 299 and the cannula 14 are movable relative to each other. The collar 299 can provide a structure disposed about a circumference of the cannula 14 (e.g., on or around an outer diameter of the cannula 14) that is configured to interact with patient tissue so as to facilitate placement of the cannula 14. For example, a face 451 of the collar 299 at the distal end of the collar can be configured to manipulate a trabecular meshwork and/or provide a guiding constraint that abuts the trabecular meshwork and/or other tissue neighboring Schlemm's canal. This guiding constraint may, for example, facilitate placement of the orifice(s) 32 to a desired penetration depth within the canal.

In the example shown in FIGS. 2A and 2B, the collar 299 is included as part of a distal portion of the sleeve 260. When the sleeve 260 and the cannula 14 are in the second configuration shown in FIG. 2B, the face 451 of the collar 299 provides a lip that protrudes radially outward away from an outer diameter of the cannula 14. The lip can abut a trabecular meshwork or other tissue neighboring Schlemm's canal so that the penetration depth of the cannula 14 is constrained or guided by a predetermined distance between the distal end of the cannula 14 and the lip (or the face 451 or distal end of the collar 299) when the device is in the second configuration.

Figure 3A:
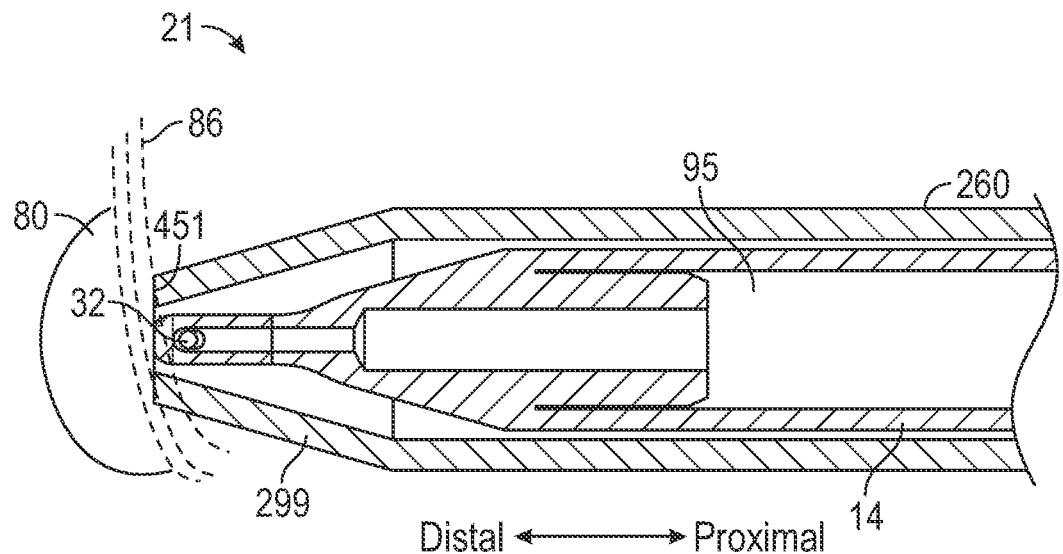
FIGS. 3A-3B are longitudinal section views showing a retractable sleeve interacting with ocular tissue.
Figure 3B:
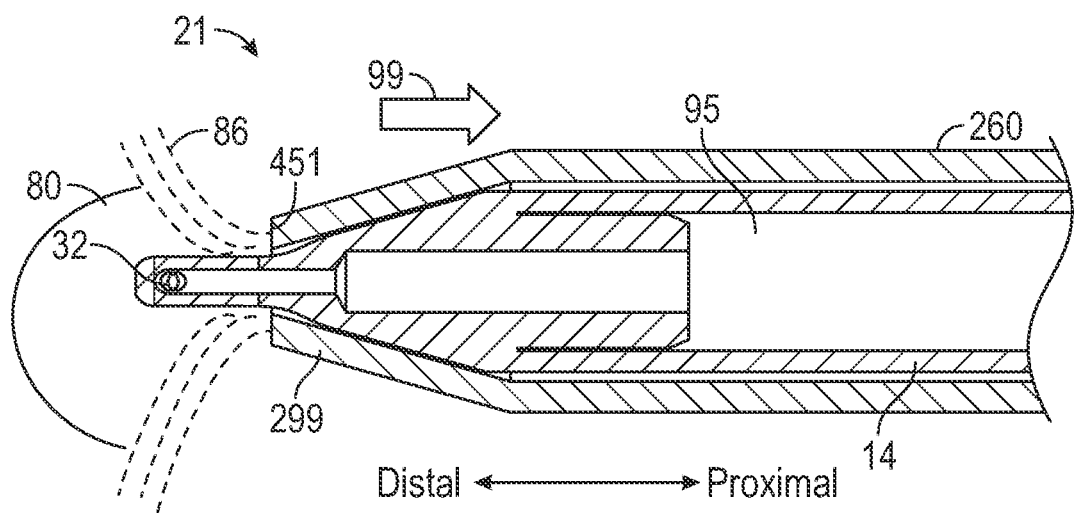

FIGS. 3A and 3B are longitudinal section views showing a distal portion 27 of an example of an ocular component 21 interacting with ocular tissue. FIG. 3A shows the sleeve 260 in a distal position, and FIG. 3B shows the sleeve 260 in a retracted position in which the sleeve 260 is retracted in a proximal direction 99 as shown by the arrow.

As shown in FIGS. 3A and 3B, the collar 299 at the distal end of the sleeve 260 can be configured to contact patient tissue, and the sleeve 260 can be configured to retract proximally so as to pull patient tissue over the cannula 14. For example, the sleeve 260 can be configured to retract in a proximal direction 99 using a snapping motion (i.e., a sharp and quick motion) so as to create a suction microenvironment over a trabecular meshwork 86 of an eye of a patient when the sleeve 260 and/or collar 299 is pressed against the trabecular meshwork 86. The sleeve 260 via its snapping motion can pull and expand the trabecular meshwork 86 proximally, which may also serve to expand a Schlemm's canal 80 as the trabecular meshwork 86 vaults away from the anterior wall of the canal. Concurrently with the pulling of the trabecular meshwork 86, the distal end of the cannula 14 may be left in place so that the trabecular meshwork 86 passes over the cannula 14 and the cannula 14 pierces or penetrates the trabecular meshwork 86, leaving the orifice(s) 32 in place inside of the Schlemm's canal 80. When the trabecular meshwork 86 is pulled and the orifice (s) 32 are positioned in the Schlemm's canal 80, the ophthalmic device 10 may be configured to deliver a substance into the Schlemm's canal 80 via a lumen 95 in the cannula 14 that is fluidly coupled to the orifice(s) 32. The proximal retraction of the sleeve 260 may beneficially serve to expand the Schlemm's canal 80 and/or otherwise facilitate fluid delivery and/or treatment via penetration by the cannula 14. It is also contemplated that the substance may be injected in some implementations by deploying the cannula 14 distally while the sleeve 260 remains in place, by moving the cannula 14 proximally or distally together with the sleeve 260, and/or by other techniques.

Figure 4A:
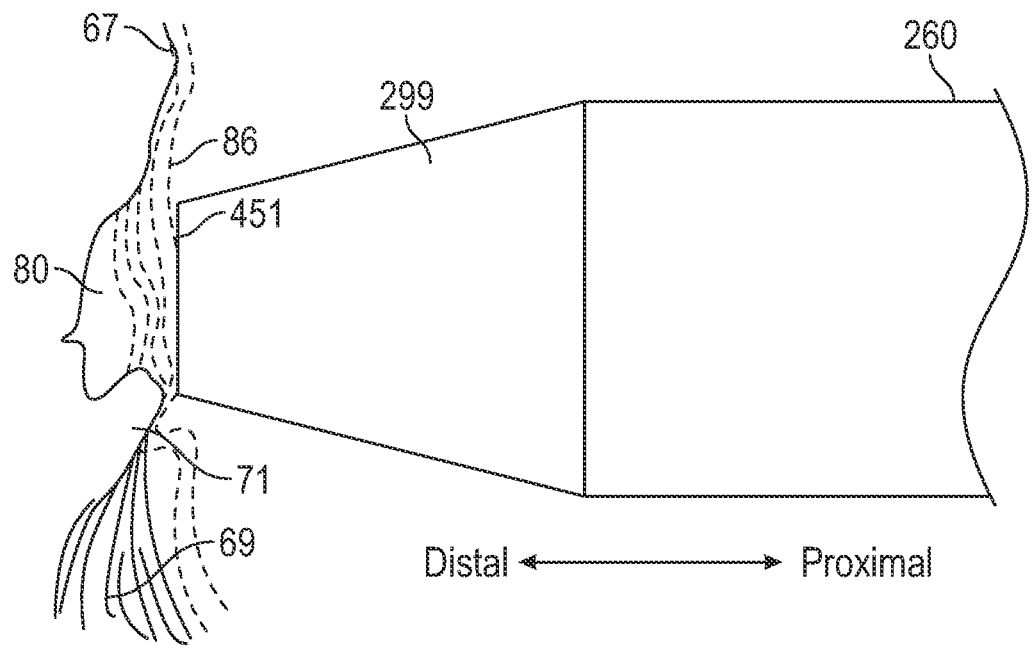
FIGS. 4A-4B are side views showing examples of sleeves interacting with ocular tissue.
Figure 4B:
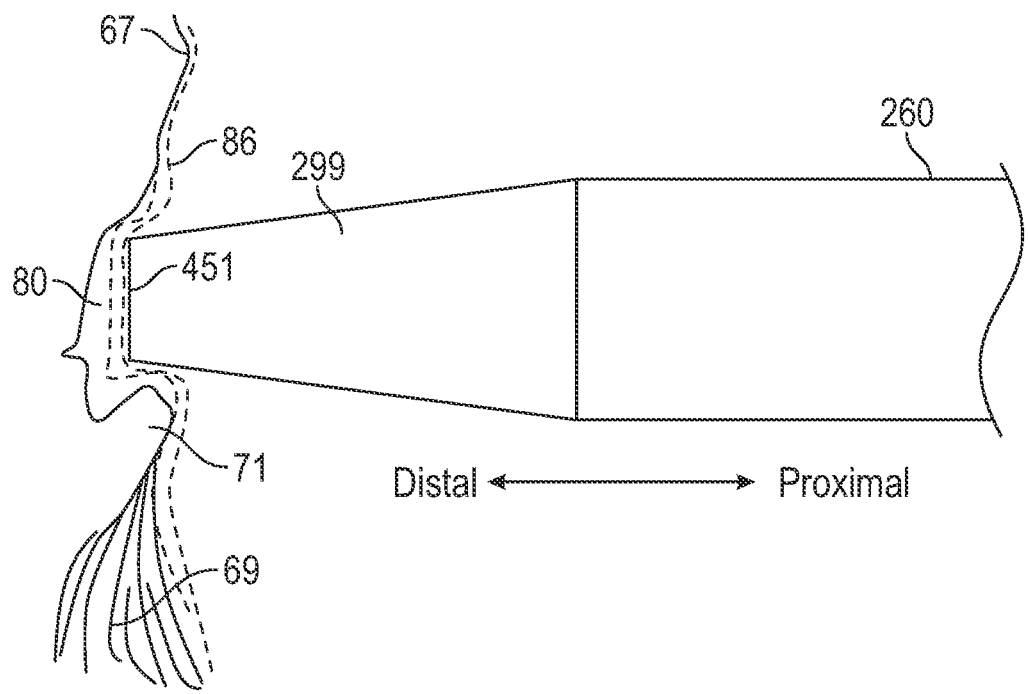

FIGS. 4A and 4B are longitudinal side views showing examples of the sleeve 260 interacting with ocular tissue. FIG. 4A shows a first example of sizing that can be implemented at the distal end of the sleeve 260, and FIG. 4B shows a second example of sizing that can be implemented in the distal end of the sleeve 260. FIGS. 4A and 4B show trabecular meshwork 86 and Schlemm's canal 80 as well as other neighboring eye anatomy, such as a scleral spur 71, ciliary muscle 69, and Schwalbe's line 67.

As shown in both FIGS. 4A and 4B, a size of a distal end of the sleeve 260 (or a size of the face 451 or distal end of the collar 299) can be sufficiently small so as to permit the distal end to be inserted in the iridocorneal angle using an ab interno approach (approach from within the anterior chamber) to abut against and contact the trabecular meshwork 86. In the example shown in FIG. 4A, the size of the distal end of the sleeve 260 is made sufficiently large so that the distal end is configured to abut against both the trabecular meshwork 86 and neighboring anatomy that is more rigid than the trabecular meshwork 86, such as scleral spur 71, so as to substantially prevent collapse of the trabecular meshwork 86 within Schlemm's canal 80 when the distal end is advanced against the trabecular meshwork 86. In the example shown in FIG. 4B, the size of the distal end of the sleeve 260 is made sufficiently small so that the distal end is configured to collapse the trabecular meshwork 86 within Schlemm's canal 80 when the distal end is pressed against the trabecular meshwork 86, e.g., in a region between scleral spur 71 and Schwalbe's line 67. In either example, upon abutting against the trabecular meshwork 86, the distal end may be configured to create a full or partial seal against the trabecular meshwork 86 and/or other ocular tissue together with surrounding fluids such as aqueous humor and/or viscoelastic (e.g., ophthalmic viscoelastic device (OVD)). The ophthalmic device 10 can then be configured to retract the sleeve 260 to pull on the trabecular meshwork 86 as described above with respect to FIGS. 3A and 3B. Further, it is contemplated that the distal end can have an oblong cross sectional shape with a long side sized like that shown in FIG. 4A and a short side sized like that shown in FIG. 4B. The long side can be configured to contact the rigid anatomy upon advancement against the trabecular meshwork 86 when the long side is oriented transverse to the direction in which the trabecular meshwork 86 extends around the lens of the eye, and the short side can be configured to collapse the trabecular meshwork 86 in the Schlemm's canal 80 when the long side is aligned with the direction in which the trabecular meshwork 86 extends.

Figure 5A:
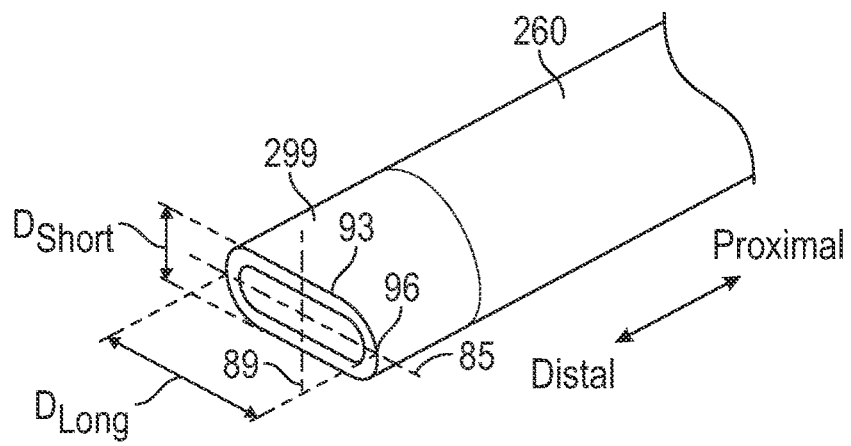
FIGS. 5A-5C are various views showing an example of a sleeve that can be included in an ophthalmic device.
Figure 5B:
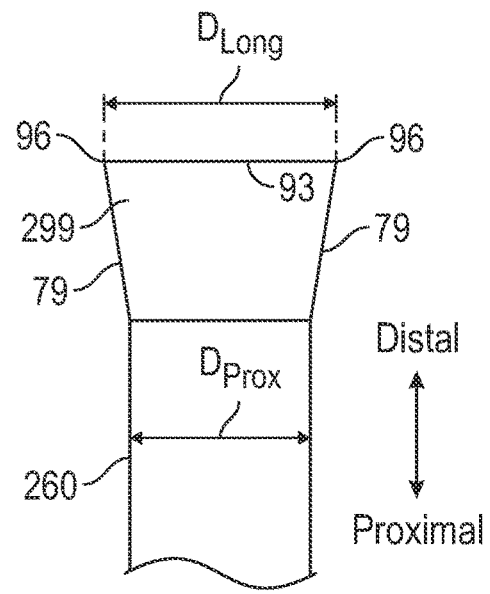
Figure 5C:
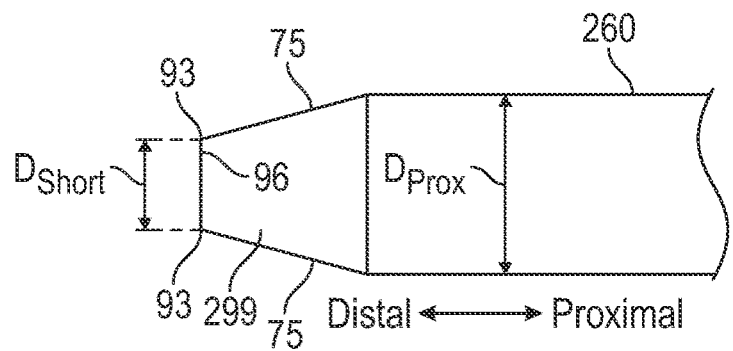

FIGS. 5A-5C are various views of a distal portion of an example of sleeve 260 including collar 299. FIG. 5A is a perspective view of the sleeve 260, FIG. 5B is a top view of the sleeve 260 as implemented in FIG. 5A, and FIG. 5C is a side view of the sleeve 260 as implemented in FIG. 5A.

As shown for example in FIGS. 5A-5C, the collar 299 (e.g., the face 451) and the distal end of the sleeve 260 can have an oblong cross-sectional shape (e.g., an oval, an ellipse, a rounded corner rectangle, or other oblong shape). The oblong shape has a pair of opposing long sides 93 and a pair of opposing short sides 96. The long sides 93 define a long axis 85 of the oblong cross-section and the oblong cross-section has a long outer diameter $D_{LONG}$ along the long axis 85. The short sides 96 define a short axis 89 of the oblong cross-section and the oblong cross-section has a short outer diameter $D_{SHORT}$ along the short axis 89 smaller than the long diameter $D_{LONG}$. As shown for example in FIG. 5B, the collar 299 and the distal end of the sleeve 260 can include a pair of diverging outer surfaces 79 on opposing sides of the sleeve 260 that diverge (or flare radially outward) towards opposing short sides of the distal end of the sleeve 260. As shown for example in FIG. 5C, the collar 299 and the distal end of the sleeve 260 can also include a pair of converging outer surfaces 75 on opposing sides of the sleeve 260 that converge (or taper radially inward) towards opposing long sides of the distal end of the sleeve 260. As a result, the long outer diameter $D_{LONG}$ can be greater than the outer diameter $D_{PROX}$ of a proximal portion of the sleeve 260, while the short outer diameter $D_{SHORT}$ can be smaller than the outer diameter $D_{PROX}$ of a proximal portion. The distal end of the sleeve 260 can be sized to fit within an iridocorneal angle (angle formed between the iris and the cornea) to permit the distal tip to contact or press against the trabecular meshwork and/or scleral spur of an eye, and the above described orientation with flared configuration along the long axis 85 can be useful to, for example, indicate a preferential orientation of the sleeve tip for the surgeon to properly place the tip to avoid over compressing the trabecular meshwork and/or Schlemm's canal.

The collar 299 and/or the sleeve 260 can further be configured as a light guide to enhance visualization when placed in the eye. For example, a light source such as one or more light emitting diode (LEDs) can be disposed in the handle 12 or otherwise positioned on the ophthalmic device 10 proximal to the distal end of the sleeve 260. The light source can be configured to couple visible light into the sidewalls of the sleeve 260 so that the light propagates through the sidewalls of the sleeve 260 via total internal reflection (TIR) and out of the distal end or distal portion of the sleeve 260 (e.g., out the face 451). Additionally or alternatively, the sleeve 260 can be made transparent or include one or more transparent windows to facilitate visualization of the sleeve 260 and/or the cannula 14, although it is contemplated that the sleeve 260 can be made wholly opaque to visible light in other implementations.

Figure 6A:
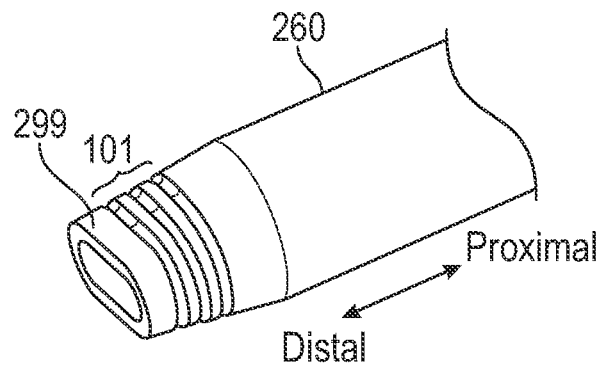
FIGS. 6A-6C are various views showing an example of a sleeve that can be included in an ophthalmic device.
Figure 6B:
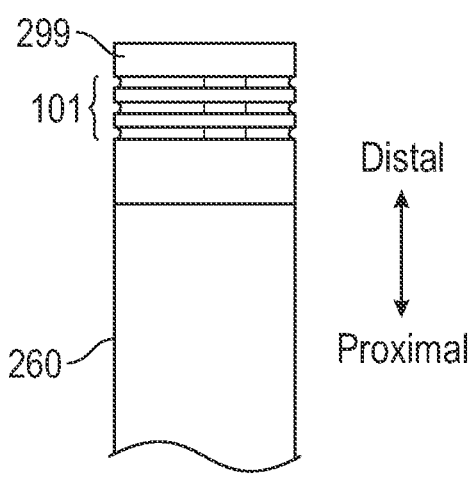
Figure 6C:
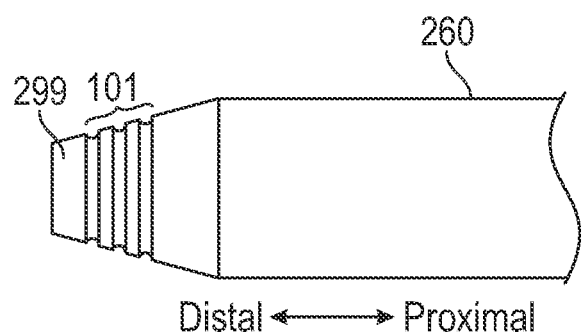

FIGS. 6A-6C are various views of a distal portion of an example of sleeve 260 including collar 299. FIG. 6A is a perspective view of the sleeve 260, FIG. 6B is a top view of the sleeve 260 as implemented in FIG. 6A, and FIG. 6C is a side view of the sleeve 260 as implemented in FIG. 6A. As shown for example in FIGS. 6A-6C, an outer surface of the collar 299 and outer surface of a distal portion of the sleeve 260 can further include grooves 101. The grooves 101 may enhance a suction effect when the sleeve 260 and collar 299 are retracted proximally by increasing a surface area of the outer surface of that contacts fluids, such as OVD or other surrounding fluids that can be disposed in the anterior chamber of the eye. The grooves 101 are shown in FIGS. 6A-6C as a plurality of circumferential grooves that extend around an outer circumference of the sleeve 260 and are disposed in a converging region of the collar 299 at a distal portion of the sleeve 260, but it is contemplated that the grooves 101 can be implemented as other types of surface area enhancing textures and/or positioned in other locations along an axial length of the sleeve.

Figure 7A:
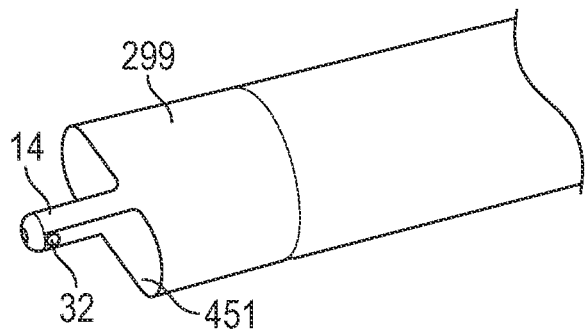
FIGS. 7A-7C are various views of an example of a cannula that can be included in an ophthalmic device.
Figure 7B:
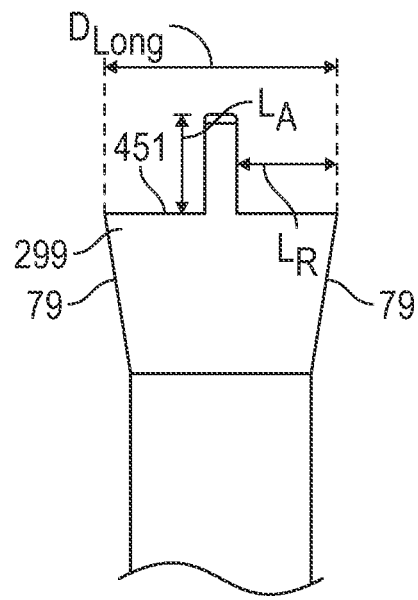
Figure 7C:
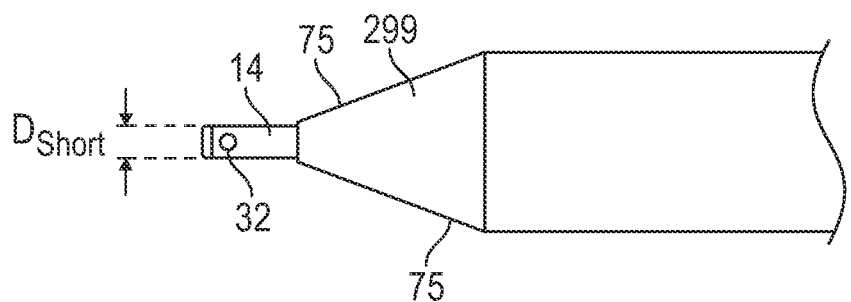

It is also contemplated, for example as shown in FIGS. 7A-7C, that the collar 299 can be fixedly coupled to the cannula 14. FIG. 7A is a perspective view of cannula 14, FIG. 7B is a top view of the cannula 14 as implemented in FIG. 7A, and FIG. 7C is a side view of cannula 14 as implemented in FIG. 7A.

In this example, an independently movable sleeve may be omitted from the ophthalmic device 10. For example, the collar 299 can be integrally formed as part of an outer portion of the cannula 14, or the collar 299 can be welded or otherwise fixedly attached to the cannula 14 so that the collar 299 moves together with the cannula 14. The fixedly coupled collar 299 can have an oblong cross-sectional shape or any of the other features described above with respect to the collar 299 when implemented on the sleeve. As shown for example in FIGS. 7A and 7B, a lip can be provided by a face of the collar 299 and protrude radially outward from a distal portion of cannula 14. The lip can thus provide a structure for interacting with tissue as described above. As shown for example in FIG. 7B, a radial length $L_R$ of lip can be approximately equal to an axial length $L_A$ of the protruding portion of the cannula 14, although it is contemplated that other dimensions may be suitably used. In this example, the lip length $L_R$ is defined by the distance between the radially outermost surface of the lip and the radially outermost surface of the axially protruding section of the cannula 14 from which the lip can extend. The cannula tip length $L_A$ is defined by the axial length from the lip (or from the face 451 or distal end of the collar 299) to the distal end of the cannula 14. The cannula 14 may have an increased diameter in a portion proximal to the collar 299 than in a portion distal to the collar 299. This may beneficially enhance rigidity or structural integrity of the cannula 14 across its working length, while permitting the distal end of the cannula 14 to be made sufficiently small in diameter for insertion into Schlemm's canal or another suitable target site of the patient. It is also contemplated that any of these dimensions or geometric features described with respect to the fixed collar shown in FIGS. 7A-7C can be suitably used in implementations where the collar is part of the sleeve 260 or otherwise movable with respect to the cannula 14 and disposed in a second configuration like that shown in FIG. 2B.

Figure 8:
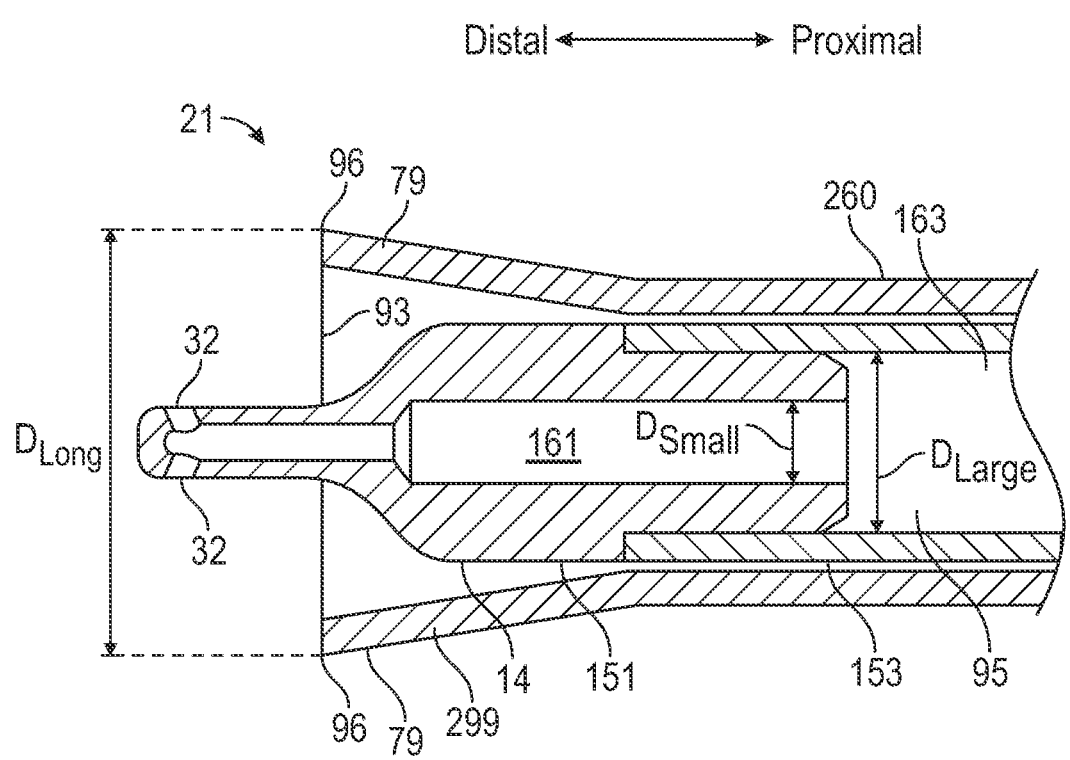
FIG. 8 is a longitudinal section view showing an example of a sleeve that can be included in an ophthalmic device.

FIG. 8 is a longitudinal section view showing a distal portion of an example of ocular component 21 that can be included in ophthalmic device 10. In the example shown in FIG. 8, the cannula 14 is shown in a protruding position relative to the sleeve 260 (e.g., in the second configuration like that shown in FIG. 2B). The cannula 14 is composed of a plurality of segments including a tip segment 151 and a proximal shaft segment 153. The tip segment 151 can be attached to the proximal shaft segment 153 by, for example, laser welding or any other suitable fastening mechanism. The tip segment 151 has an inner diameter $D_{SMALL}$ and the proximal shaft 153 has an inner diameter $D_{LARGE}$ that is greater than the inner diameter $D_{SMALL}$ of the tip segment 151. Accordingly, the lumen 95 extending through the cannula 14 is segmented to have a proximal portion 163 that is larger in diameter than the distal portion 161. This can, for example, reduce back pressure in the device, although implementations are also contemplated in which the cannula 14 is composed of a single piece or integral construction, and/or in which the lumen 96 has a substantially constant diameter through the cannula 14.

FIG. 8 also shows the collar 299 configured as shown in the example of FIGS. 5A-5C, in which the collar 299 is implemented at the distal end of the sleeve 260 so that a distal tip of the sleeve 260 has an oblong cross section with flared diverging outer surfaces 79 on opposing sides of the sleeve 260. As shown in the example of FIG. 8, the one or more orifices 32 can include a pair of orifices on opposing sides of the cannula 14 (e.g., oriented approximately 180 degrees apart from one another about the circumference of the cannula 14). The pair of opposing orifices can be aligned along the long axis 85 of the distal tip (aligned along the long axis of the oblong cross section of the collar 299) so that the orifices 32 face the short sides 96 of the sleeve distal end and face the diverging outer surfaces 79. This can, for example, allow the flared or diverging surfaces to serve as an indicator for bringing the orifices of the cannula 14 into the Schlemm's canal with an orientation that points the injected fluid towards the direction of extent of the canal. Although shown in an implementation in which the collar 299 is fixedly coupled to a movable sleeve 260, it is also contemplated that this orientation of the orifices 32 can be applied to implementations in which the collar 299 is fixed to the cannula 14 like in the example of FIGS. 7A-7C.

Figure 9A:
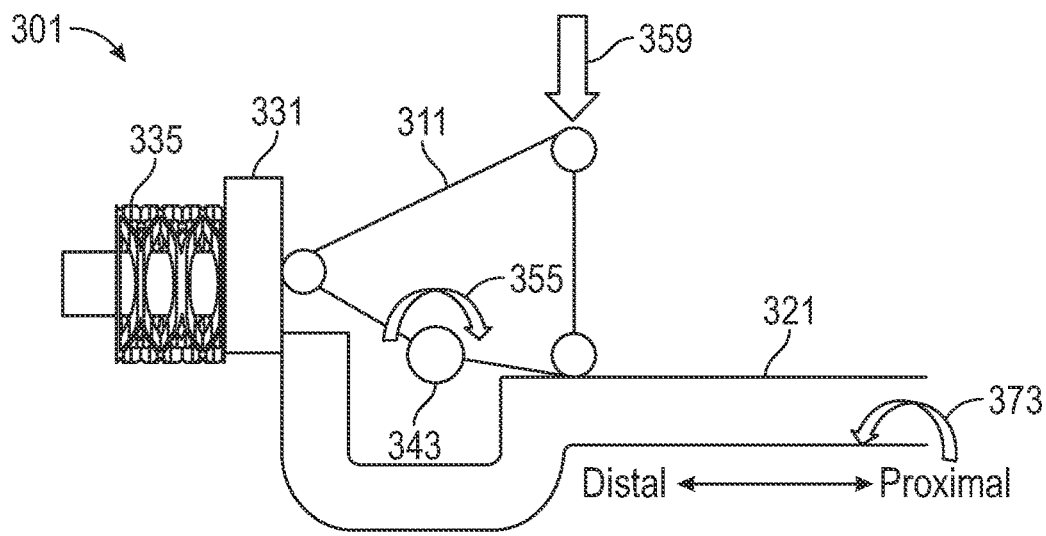
FIGS. 9A-9C are side views showing an example of a mechanism that can be configured to retract a sleeve in an ophthalmic device.
Figure 9B:
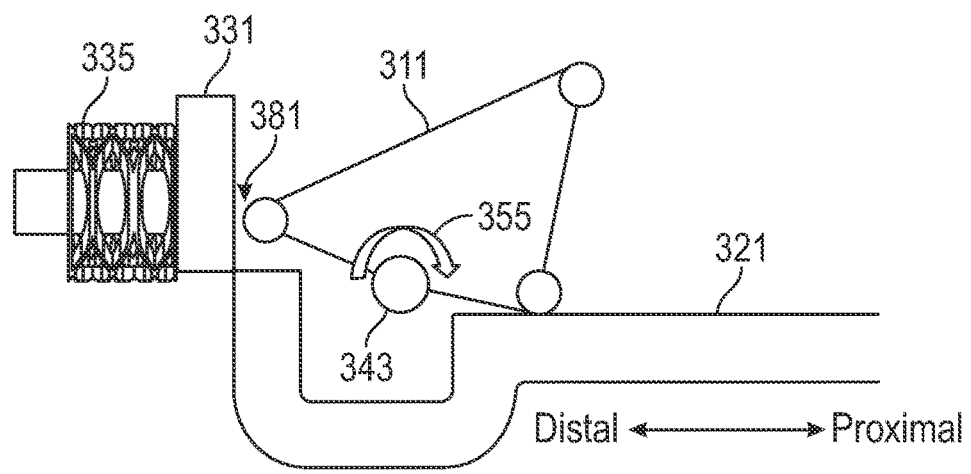
Figure 9C:
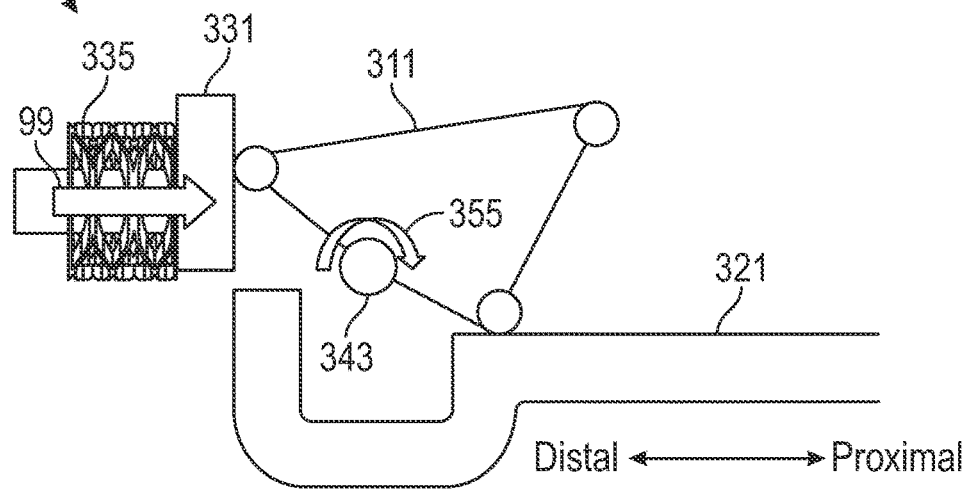

FIGS. 9A-9C are side views showing an example of an internal mechanism 301 that can be included in the ophthalmic device 10 and utilized to retract sleeve 260. The internal mechanism 301 can, for example, be disposed in an internal volume of the handle 12 and coupled to the actuator 38.

FIG. 9A shows the internal mechanism 301 in an initial loaded state, FIG. 9B shows the internal mechanism 301 in an intermediate state, and FIG. 9C shows the internal mechanism 301 in a released state during or after retraction of the sleeve 260. The internal mechanism 301 shown in FIGS. 9A-9C utilizes a cam and follower system to retract sleeve 260 in a proximal direction 99 relative to the cannula 14 and relative to the handle 12 (sleeve 260, cannula 14, and handle 12 not visible in FIGS. 9A-9C). More particularly, the internal mechanism 301 includes a cam 311 coupled to a catch 321 and a spring-loaded follower 331. The follower 331 can be fixedly coupled to the sleeve 260 so that the sleeve 260 moves together with the follower 331. The catch 321 is configured to hold the follower 331 in a distal position, and the cam 311 is configured to move the catch 321 to release the follower 331 in a proximal direction 99. The cam 311 can be coupled to a push button (such as that shown in FIG. 1) to permit the cam 311 to be moved or actuated by the push button.

In FIG. 9A, the internal mechanism 301 is shown in an initial state. In this state, the follower 331 (and the sleeve 260) are in a distal position. The catch 321 is in a first position in which it holds the follower in the distal position by, for example, abutting a proximal surface of the follower 331 to prevent or restrict proximal movement of the follower 331. While the catch is in the first position and the follower is in the distal position, a spring 335 applies a spring force to the follower 331 in a proximal direction 99. The spring 335 is shown in FIGS. 9A-9C as an axial compression spring, but it will be appreciated that a variety of other springs can be suitably used. The push button (not visible in FIG. 9A) can be coupled to the cam 311 and is in an un-pressed position (e.g., an upper position) when the internal mechanism 301 is in the initial state. Application of a user force to the push button can urge rotational movement of the cam 311 in a first cam rotational direction 355 about cam pivot point 343. As the cam 311 rotates in the first cam rotational direction 355, the cam 311 rotates against the catch 321 to urge movement of the catch 321, for example, to flex in a direction 373 away from the first position of the catch and towards a second position of the catch.

In FIG. 9B, the internal mechanism 301 is shown in an intermediate state as the above forces are being applied. As shown in FIG. 9B, a gap 381 can be formed between the cam 311 and the follower 331 upon rotation of the cam 311 in the first rotational direction 355. For example, as the cam 311 rotates against the catch 321, the catch 321 can continue to hold the follower 331 in a distal position while the cam 311 rotates away from the follower 331 in the first cam rotational direction 355. The gap 381 can provide a clearance for the follower 331, together with the sleeve 260, to freely move so that potential energy held in the spring 335 can cause a quick and sharp snapping motion upon release of the follower 331 by the catch 321.

In FIG. 9C, the internal mechanism 301 is shown in a retracted or retracting state in which the follower 331 is released by the catch 321. As shown in FIG. 9C, upon sufficient rotation of the cam 311 against the catch 321, the cam 311 can release the follower 331 by, for example, moving the catch 321 to a second position in which the catch 321 releases the follower 331 by, for example, removing a restriction with which a distal surface of the catch 321 abuts against a proximal surface of the follower 331. Upon release of the follower, potential energy stored in the spring 335 is released to urge proximal motion of the follower 331 (and thus the sleeve 260) in the proximal direction 99. The follower 331 can move freely through the gap 381 to a proximal position until it is stopped by a restriction. For example, the proximal motion of the follower 331 can terminate upon the follower 331 abutting the cam 311, upon abutting a stop included in a housing of the handle 12 (not visible in FIG. 9C), and/or upon abutting a stop included on the catch 321. The surface that provides a stop for the follower 331 can, for example, be relatively rigid or can include a cushion or energy absorbing member so as to soften an impact and prevent shocks from transmitting through the device and to a surgeon's hand.

In FIG. 9C, the catch 321 is shown in a second position (released position). The catch 321 can be biased to the first position (abutting position shown in FIG. 9A) so as to permit the internal mechanism 301 to be reset to the initial state upon, for example, release of the push button by a user. For example, after retraction of the follower 331, upon release of the push button, the bias of the catch 321 towards the first position can cause the catch 321 to move upwards to urge rotational movement of the cam 311 in a second cam rotational direction opposite to the first cam rotational direction 355. As the catch 321 urges the rotation of the cam 311 in the opposite direction, the cam 311 urges the follower 331 (or the catch 321 urges the follower via the cam 311) in a distal direction so as to move the follower 331 from the follower proximal position to the follower distal position to reload the spring 335. As the catch 321 urges the rotation of the cam 311 and moves the follower 331 in this manner, the catch 321 can also return to the first position where it abuts the follower 331 to hold the follower 331 in the distal position. The internal mechanism 301 can then be operated again in a similar fashion for one or more repeated sleeve retractions.

While the mechanism has been described with respect to implementations in which the internal mechanism 301 is utilized to retract sleeve 260 (e.g., to pull a trabecular meshwork via a snapping motion like that described above with respect to the example of FIGS. 3A-3B), it will be appreciated that the mechanism may be suitably used for other modes of operation. For example, the snapping motion created by the mechanism can be utilized to snap the cannula 14 and/or sleeve 26 proximally and/or distally to create a vibration (e.g., upon impact of the follower 331 against a stop) that facilitates penetration of the trabecular meshwork without a need for a suction effect. Thus, the follower 331 can be fixedly coupled to the cannula 14 or any other suitable component for which motion is desired. It will also be appreciated that if the mechanism is employed for distal motion of the sleeve 260, cannula 14, or any other component, the various parts and operation of the mechanism can be reversed. It is further contemplated that other mechanisms, such as magnetic actuators or other types of spring loaded actuators can be employed for retraction of the sleeve 260.

Figure 10:
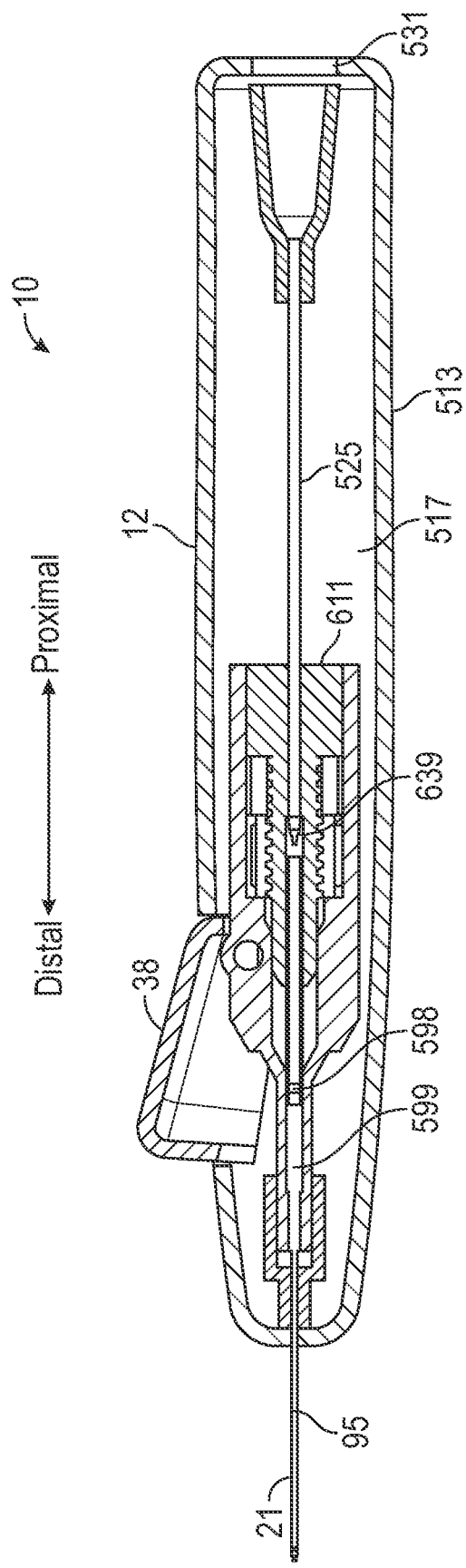
FIG. 10 is a longitudinal section view showing an example of an ophthalmic device.

FIG. 10 is a longitudinal section view showing an example of ophthalmic device 10. FIG. 10 shows an example of a structure for handle 12 and a fluid delivery mechanism that can be included in the handle 12 to facilitate delivery of a substance through the ocular component 21.

As shown in FIG. 10, the handle 12 can include a housing 513 that encloses and defines an internal volume 517. A lumen 525 (sometimes referred to herein as "handle lumen") can be disposed in the handle 12 and be fluidly coupled to the lumen 95 (sometimes referred to herein as "cannula lumen") protruding from the distal end of the handle 12. The handle lumen 525 can, for example, extend through the internal volume 517 and be configured to deliver fluid to the cannula lumen 95 from a fluid source, such as a fluid reservoir disposed within the internal volume or coupled to the handle externally.

As shown for example in FIG. 10, the handle 12 can include an inlet port 531 configured to couple to the fluid source and to receive an inlet fluid. The inlet port 531 can, for example, include a luer lock connector or any other suitable connector configured to connect to a viscoelastic syringe or any other suitable fluid reservoir. The inlet port 531 is shown in FIG. 10 disposed on a proximal end of the handle 12 so as to provide an inlet channel extending through an opening in a proximal end of the handle housing 513. Additionally or alternatively, the inlet port 531 can be disposed on another location on the handle 12, such as on a lateral sidewall of the handle 12. In the example shown in FIG. 10, the handle 12 holds a reservoir 599 that can be filled with an initial volume of fluid or other substance via the inlet port 531.

The handle 12 shown in FIG. 10 further includes a pump 611 which can be configured to move fluid through the handle lumen 525 and/or through the cannula lumen 95. For example as shown in FIG. 10, the pump 611 can include or be coupled to a piston 598 disposed within the internal volume 517 of the handle 12 and configured to translate in an axial direction proximally and/or distally. The piston pump can be configured to move in the distal direction from a proximal pump position to a distal pump position to draw fluid from the inlet port 531 and/or to urge or push fluid out through the distal end of the cannula lumen 95 and out through the orifice(s) 32. Thus, the pump 611 can be configured for positive and/or negative displacement of fluid. The piston 598 can also, for example, be reciprocal in the housing and configured to move in a proximal direction, from the distal pump position to the proximal pump position, so as to reset for delivering a subsequent dosage of fluid. Alternatively, the piston 598 can be configured to move incrementally in a distal direction in which each increment of distal motion corresponds to a dosage of fluid or other substance.

The pump 611 can include or be coupled to a valve 639 which can be disposed in the fluidic pathway of the handle lumen 525 and be fixedly coupled to the pump 611 so as to move together with the pump 611. The valve 639 can, for example, be implemented as or otherwise include a one-way valve (or "check valve") that permits fluid motion there through in a distal direction and restricts fluid motion there through in a proximal direction so as to create suction from the inlet port 531 and to force fluid out of the orifice(s) upon distal motion of the valve 639 together with the handle 12. Additionally or alternatively, it will be appreciated that various other types of pumps and/or fluid transfer mechanisms can be configured to move the fluid through the ophthalmic device 10.

The pump 611 can further be coupled to actuator 38 so as to permit actuation of the pump for delivery of a dosage or amount of fluid upon actuation of the actuator 38. The pump 611 can, for example, be coupled to the same actuator that moves the sleeve 260 or other part of the ocular component 21, or the pump 611 can be coupled to a separate actuator from that used to move the ocular component 21. In the example shown in FIG. 10, the actuator 38 includes a push button coupled to the pump 611 and configured trigger delivery of a discrete dosage of fluid upon user depression of the push button.

Figure 11A:
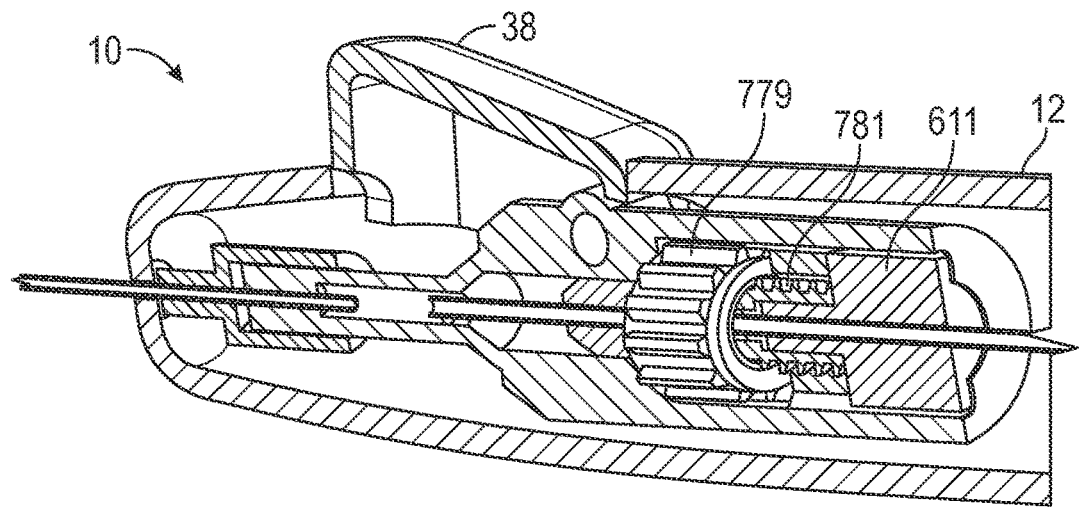
FIGS. 11A-11C are cutaway views showing an example of a mechanism configured to inject a fluid.
Figure 11B:
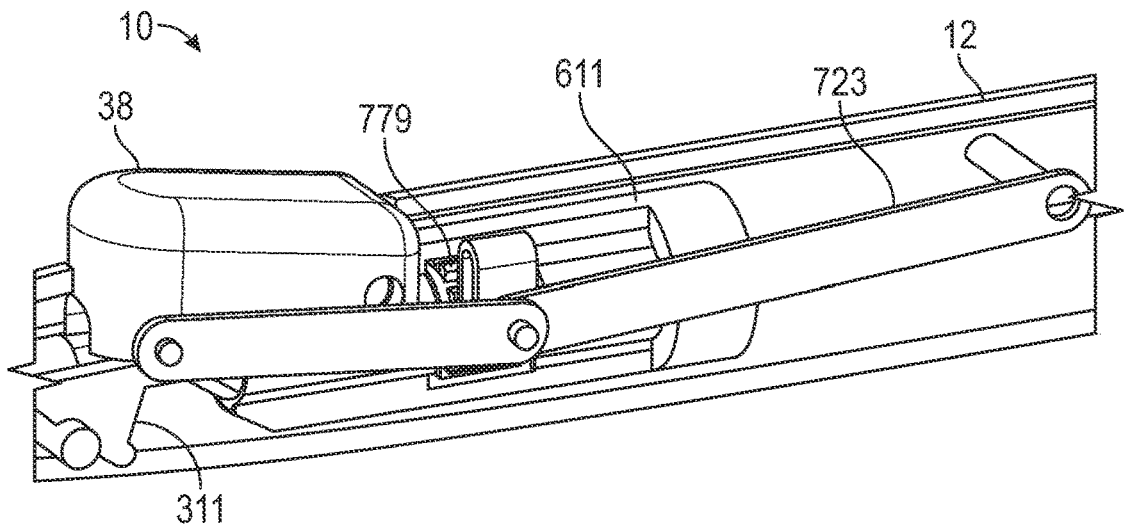
Figure 11C:
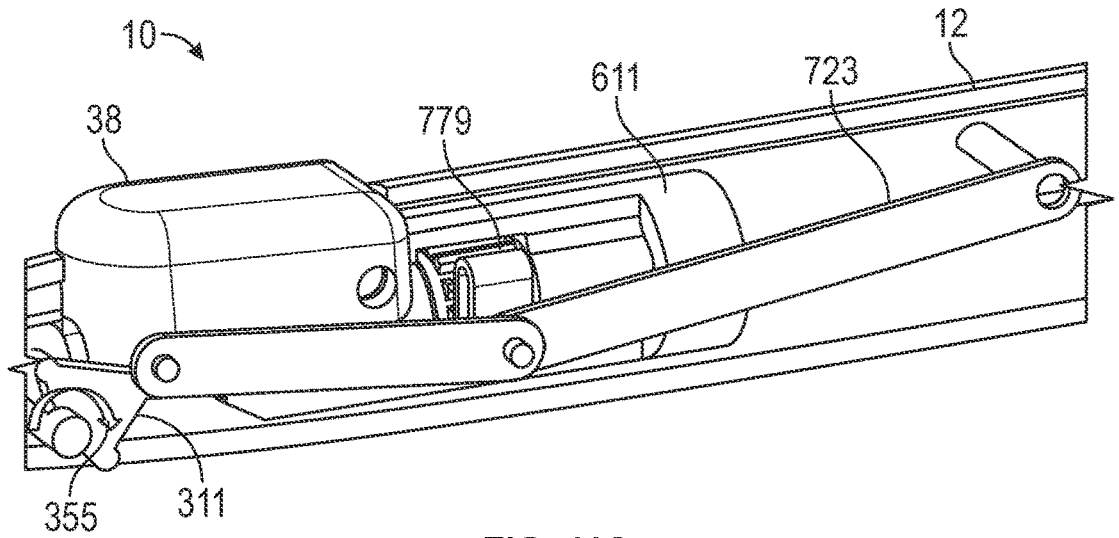

FIGS. 11A-11C are cutaway views of the handle 12 of ophthalmic device 10 in which the actuator 38 is configured to actuate motion of the distal ocular component as well as the pump 611 in concert with each other. FIG. 11A is a cutaway view showing the internal mechanism with a linkage and cam removed for clarity. FIGS. 11B and 11C are cutaway views showing the internal mechanism with linkage 723 and cam 311 illustrated in an initial position before button press, and in an actuated position after button press, respectively.

The mechanism shown in FIGS. 11A-11C can be used so that each button press of the actuator 38 is a trigger that causes both retraction of the sleeve 260 (e.g., to pull trabecular meshwork 86 over the cannula 14 as shown in FIGS. 3A-3B) and delivery of a dosage of fluid through the cannula 14 while the sleeve 260 is retracted (e.g., while the trabecular meshwork 86 is pulled over the cannula 14 and the orifice(s) 32 are positioned within the Schlemm's canal 80 as shown in FIGS. 3A-3B). As shown for example in FIG. 11A, the mechanism can include a nut 779 coupled to a threaded portion 781 which is included in or fixedly coupled to the pump 611. The nut 779 can be mated with the threaded portion 781 so that rotation of the nut 779 drives axial motion of the pump 611 (e.g., translation in a distal direction) so as to cause the pump 611 to move fluid through the handle 12.

As shown in FIGS. 11B and 11C, the actuator 38 can be implemented as a push button coupled to the nut 779 via a linkage 723. As shown in FIGS. 11B and 11C, the same push button that drives the nut 779 can also be coupled to cam 311, directly or via the linkage 723. Upon a user force depressing the button from the un-pressed position shown in FIG. 11B to the pressed position shown in FIG. 11C, the push button can drive rotation of the cam in the first rotational direction 355 (e.g., to retract sleeve 260) and drive rotation of the nut 779 via the linkage 723, so as to move the piston 598 incrementally forward distally to move fluid through the handle 12 via positive displacement. Concurrently, the rotation of the cam 311 causes retraction of the sleeve 260 so the substance is delivered by the pump 611 while the sleeve 260 is in a retracted proximal position.

Figure 12A:
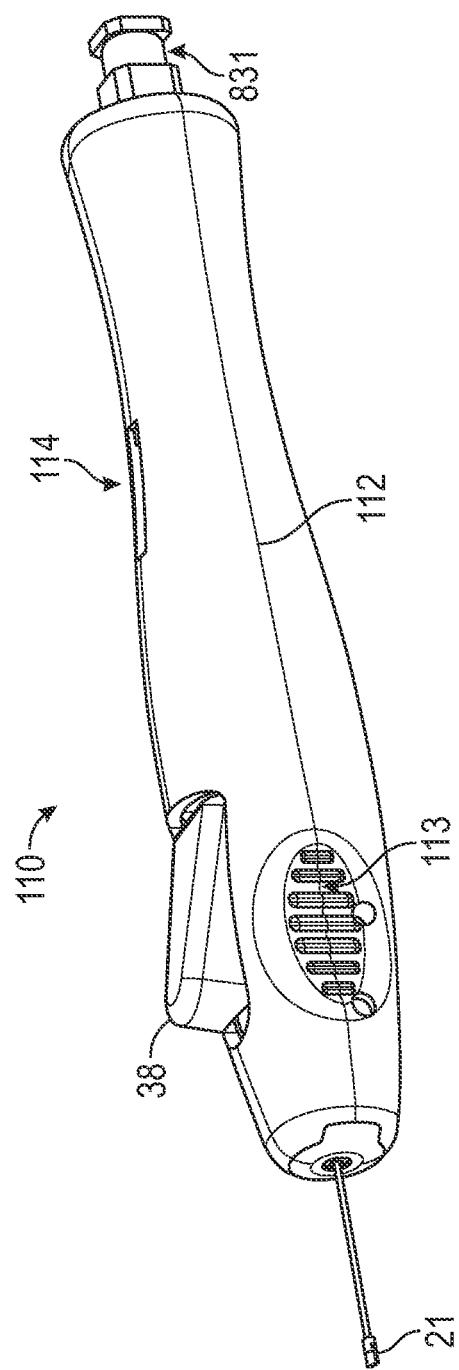
FIG. 12A is a perspective view of an example of an ophthalmic device.
Figure 12B:
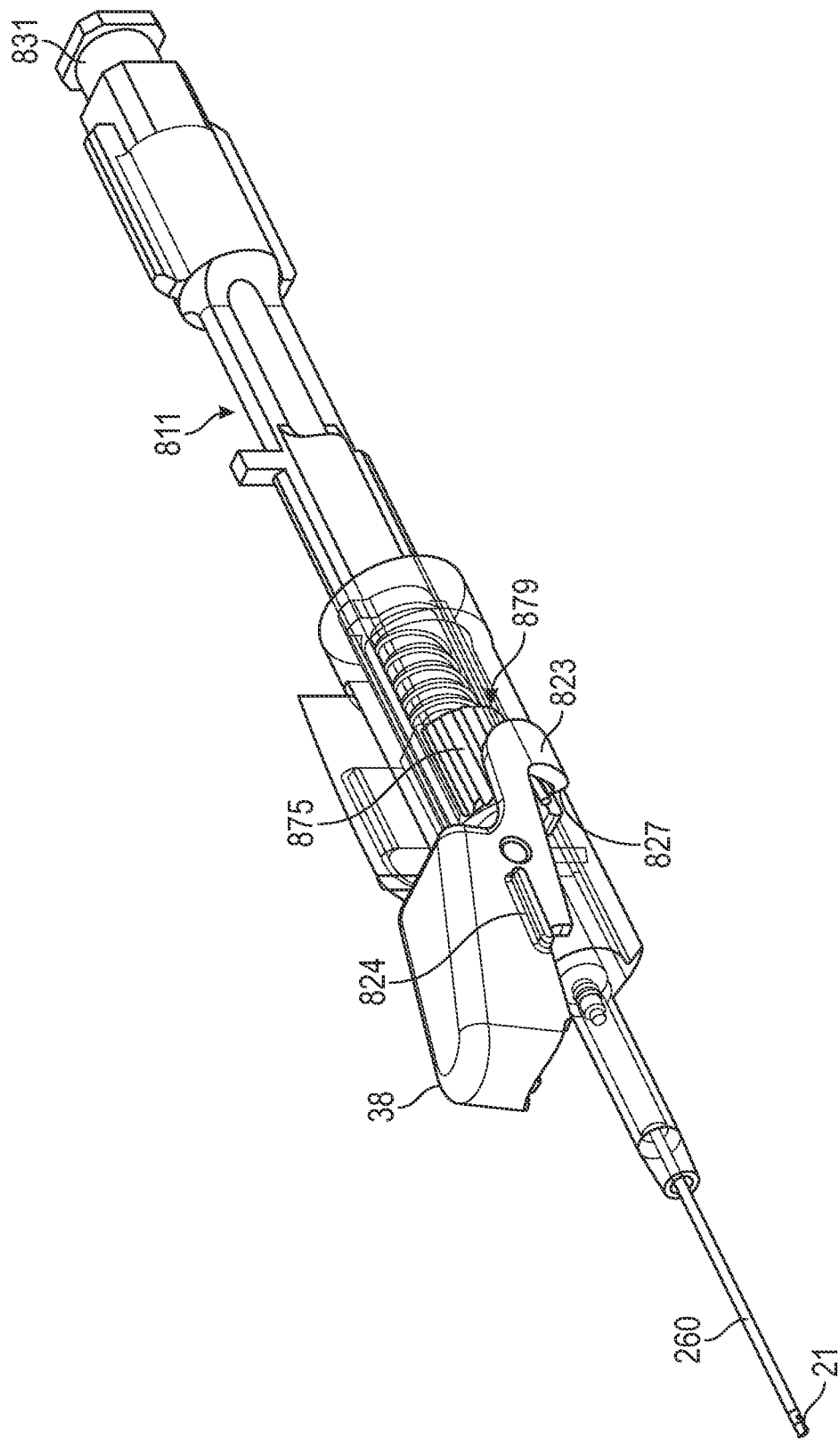

FIGS. 12A-12F illustrate an ophthalmic device 110 in which an actuator is configured to actuate motion of a distal ocular component as well as a pump in concert with each other. FIG. 12A shows a perspective view of ophthalmic device 110. FIGS. 12B and 12C show perspective and sectional views of internal components of the ophthalmic device 110. FIGS. 12D-12F show various views of portions of the internal components during actuation of ophthalmic device 110.

Referring to FIG. 12A, ophthalmic device 110 has many of the same components as ophthalmic device 10, which are numbered the same for consistency. Ophthalmic device 110 can include a handle 112 coupled to the ocular component 21. The handle 112 may be sized and shaped to provide easy gripping by a healthcare provider (e.g., ophthalmic surgeon) with minimum stress on the healthcare provider's hand. An outer surface of the handle 112 includes finger grips 113 having a contoured shape and a ribbed surface to facilitate grasping of the handle 112 by the user. The actuator 38 is a mechanical push button disposed on the handle 112 and movable between an un-pressed and pressed position. The handle 112 may include a viewing port 114 (e.g., a dispensing volume indicator), or the handle 112 may be essentially opaque with no viewing port. The handle 112 can include an inlet port 831 configured to couple to the fluid source and to receive an inlet fluid. The inlet port 831 may include any of the configurations and/or features of inlet port 531.

The internal components shown in FIGS. 12B and 12C can be used so that each button press of the actuator 38 is a trigger that causes both retraction of the sleeve 260 (e.g., to pull trabecular meshwork 86 over the cannula 14 as shown in FIGS. 3A-3B) and delivery of a dosage of fluid through the cannula 14 while the sleeve 260 is retracted (e.g., while the trabecular meshwork 86 is pulled over the cannula 14 and the orifice(s) 32 are positioned within the Schlemm's canal 80 as shown in FIGS. 3A-3B). As shown for example in FIGS. 12B and 12C, the internal components can include a drive nut 879 coupled to a threaded portion 881, which is included in or fixedly coupled to a plunger 811 (e.g., pump). The drive nut 879 can be mated with the threaded portion 881 so that rotation of the drive nut 879 drives axial motion of the plunger 811 (e.g., translation in a distal direction) so as to cause the plunger 811 to move fluid through the handle 112.

As shown in FIGS. 12B-12F, the actuator 38 can be implemented as a push button coupled to the drive nut 879 via a linkage arm 823. The drive nut 879 may have multiple teeth 875, each tooth 875 having a flat portion 876 and a sloped portion 877. The linkage arm 823 may have an engagement portion 827 that is sized and shaped to grab onto the flat portion 876 of a tooth 875. The same push button 38 that drives the drive nut 879 can also be coupled to cam 311 via a protrusion 824. Upon a user force 850 depressing the button 38 from the un-pressed position shown in FIG. 12D, the button 38 may rotate about an actuator axle 39, causing the protrusion 824 to push down on the cam 311 and the linkage arm 823 to pull up on the tooth 875 of the drive nut 879 to which the linkage arm 823 is engaged. Accordingly, the button 38 can drive rotation of the cam 311 via the protrusion 824 in the first rotational direction 355 (e.g., to retract sleeve 260) and drive rotation of the drive nut 879 in a drive rotational direction 855 (e.g., counterclockwise) via the linkage arm 823, so as to move a plunger tube 898 incrementally forward (e.g., distally) a stroke length 870 to move fluid through the handle 112 via positive displacement. The plunger tube 898 may have a plunger seal 899 (e.g., a wavy seal) to prevent backflow of the substance. Concurrently with the drive nut 879 rotation, the rotation of the cam 311 causes retraction of the sleeve 260 so the substance is delivered by the plunger 811 while the sleeve 260 is in a retracted proximal position.

As shown in FIG. 12F, a side panel shim 890 may engage with the teeth 875 of the drive nut 879 in a ratchet process. For example, as the drive nut 879 rotates in the drive rotational direction 855, an engagement portion 891 of the side panel shim 890 may ride up the sloped portion 877 of a tooth 875 and then drop down along the trailing flat portion 876 of the tooth 875, thus allowing the drive nut 879 to rotate in the drive rotational direction 855 with little or no resistance. However, when the engagement portion 891 of the side panel shim 890 is engaged with the flat portion 876 of a tooth 875, the side panel shim 890 resists rotation of the drive nut 879 in the opposite rotational direction (e.g., clockwise).

Figure 13A:
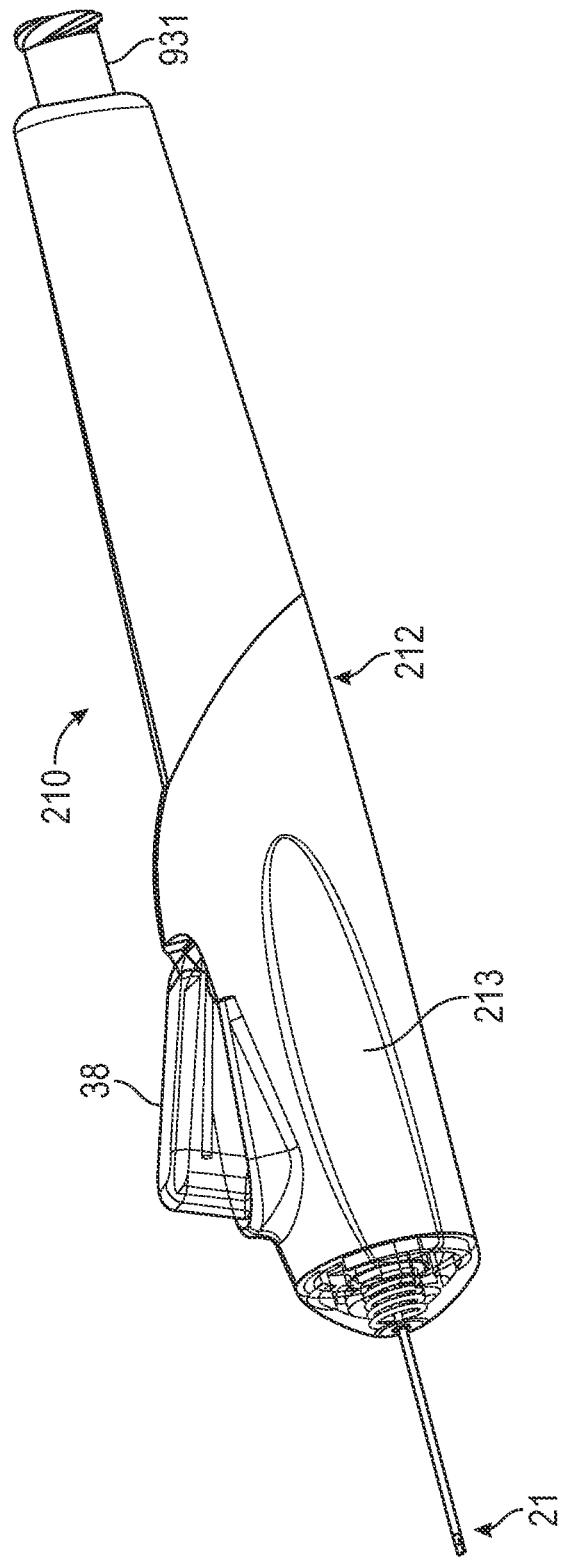
FIG. 13A is a longitudinal section view showing an example of an ophthalmic device.
Figure 13B:
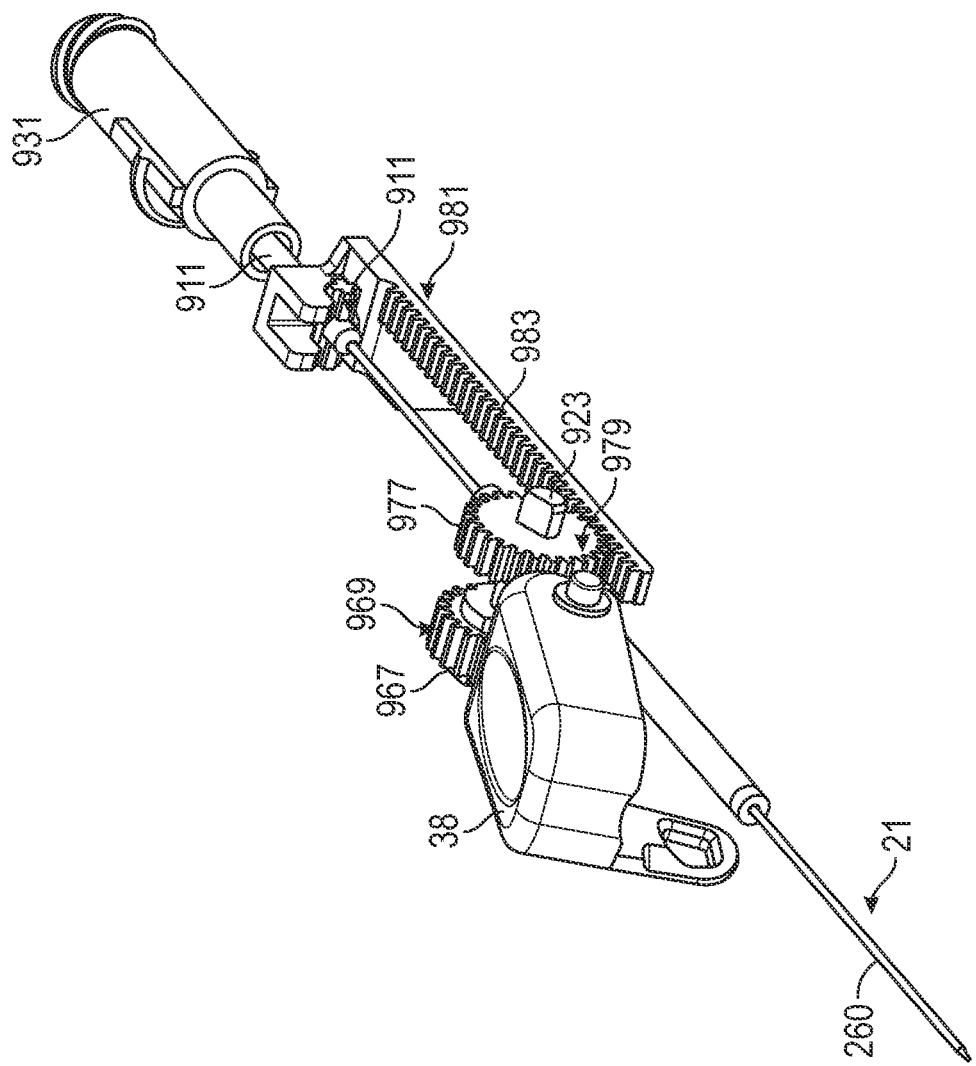
Figure 13D:
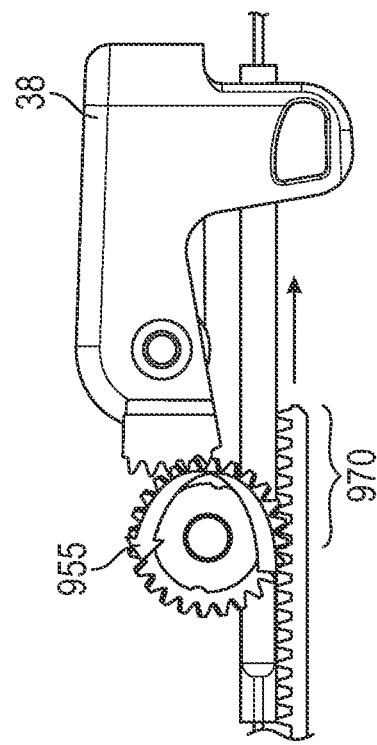
FIGS. 13D-13G are sectional portion views of internal components of the ophthalmic device of FIG. 13A, illustrating component action during actuation.

FIGS. 13A-13G illustrate an ophthalmic device 210 in which an actuator is configured to actuate motion of a distal ocular component as well as a pump in concert with each other. FIG. 13A shows a perspective view of ophthalmic device 210. FIGS. 13B and 13C show perspective and sectional views of internal components of the ophthalmic device 210. FIGS. 13D-13G show views of portions of the internal components during actuation of ophthalmic device 210.

Referring to FIG. 13A, ophthalmic device 210 has many of the same components as ophthalmic device 10, which are numbered the same for consistency. Ophthalmic device 210 can include a handle 212 coupled to the ocular component 21. The handle 212 may be sized and shaped to provide easy gripping by a healthcare provider (e.g., ophthalmic surgeon) with minimum stress on the healthcare provider's hand. An outer surface of the handle 212 may include finger grips 213 having a contoured shape and a ribbed surface to facilitate grasping of the handle 212 by the user. The actuator 38 is a mechanical push button disposed on the handle 212 and movable between an un-pressed and pressed position. The handle 212 may include a viewing port (not shown), or the handle 212 may be essentially opaque with no viewing port. The handle 212 can include an inlet port 931 configured to couple to the fluid source and to receive an inlet fluid. The inlet port 931 may include any of the configurations and/or features of inlet port 531.

The internal components shown in FIGS. 13B and 13C can be used so that each button press of the actuator 38 is a trigger that causes both retraction of the sleeve 260 (e.g., to pull trabecular meshwork 86 over the cannula 14 as shown in FIGS. 3A-3B) and delivery of a dosage of fluid through the cannula 14 while the sleeve 260 is retracted (e.g., while the trabecular meshwork 86 is pulled over the cannula 14 and the orifice(s) 32 are positioned within the Schlemm's canal 80 as shown in FIGS. 3A-3B). As shown for example in FIGS. 13B and 13C, the internal components can include a drive gear 979 coupled to a rack portion 981, which is included in or fixedly coupled to a plunger 911 (e.g., pump). Drive gear teeth 977 can be engaged with rack portion teeth 983 so that rotation of the drive gear 979 drives axial motion of the plunger 911 (e.g., translation in a distal direction) so as to cause the plunger 911 to move fluid through the handle 212.

As shown in FIGS. 13B-13G, the actuator 38 can be implemented as a push button coupled to a trigger gear 969. Trigger gear teeth 967 can be engaged with actuator teeth 37 and the trigger gear 969 can be rotated by pushing down on the actuator 38. The trigger gear 969 can be coupled to the drive gear 979 via a drive axle 923. The trigger gear 969 can also be coupled to a sleeve follower 971 via a cam portion 31. Upon a user force 850 depressing the button 38 from the un-pressed position shown in FIG. 13D, the button 38 may cause the cam portion 31 to rotate the sleeve follower 971 so that a hill portion 972 of the sleeve follower 971 rotates to a valley portion 973 of the sleeve follower 971, causing the sleeve 260 to snap back (e.g., proximally) to retract the sleeve 260. Depressing the button 38 from the un-pressed position shown in FIG. 13D may also cause the trigger gear 969 to rotate the drive axle 923, further causing the drive gear 979 to rotate. Accordingly, the button 38 can drive rotation of the drive gear 979 via the drive axle 923 in a drive rotational direction 955 to drive movement of the rack portion 981, so as to move the plunger 911 incrementally forward (e.g., distally) a stroke length 970 to move fluid through the handle 212 via positive displacement. The plunger 911 may have a rear seal 999 (e.g., O-ring seal). Concurrently with the drive gear 979 rotation, the movement of the cam portion 31 causes retraction of the sleeve 260. The substance is delivered by the plunger 911 beginning with actuation of the actuator 38 and through retraction of the sleeve 260 in a proximal position.

Figure 13F:
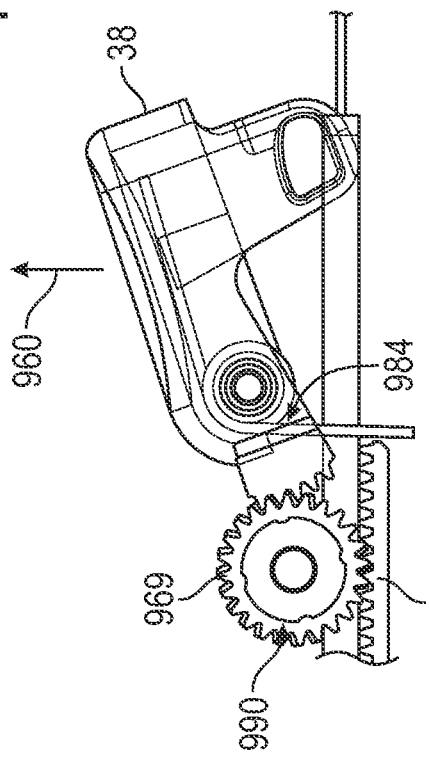
Figure 13E:
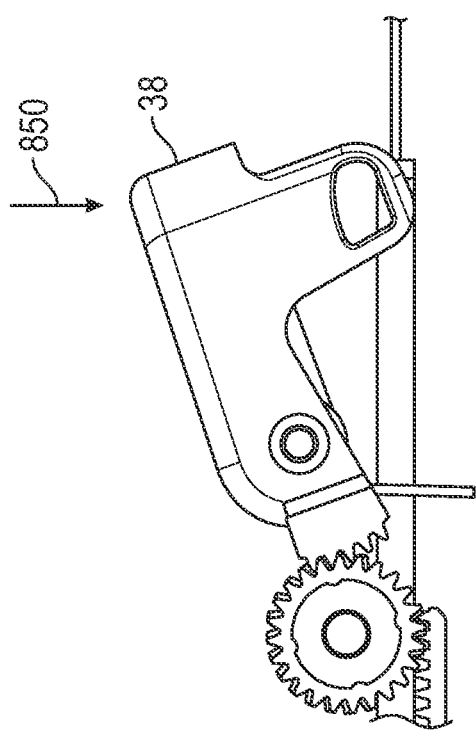
Figure 13G:
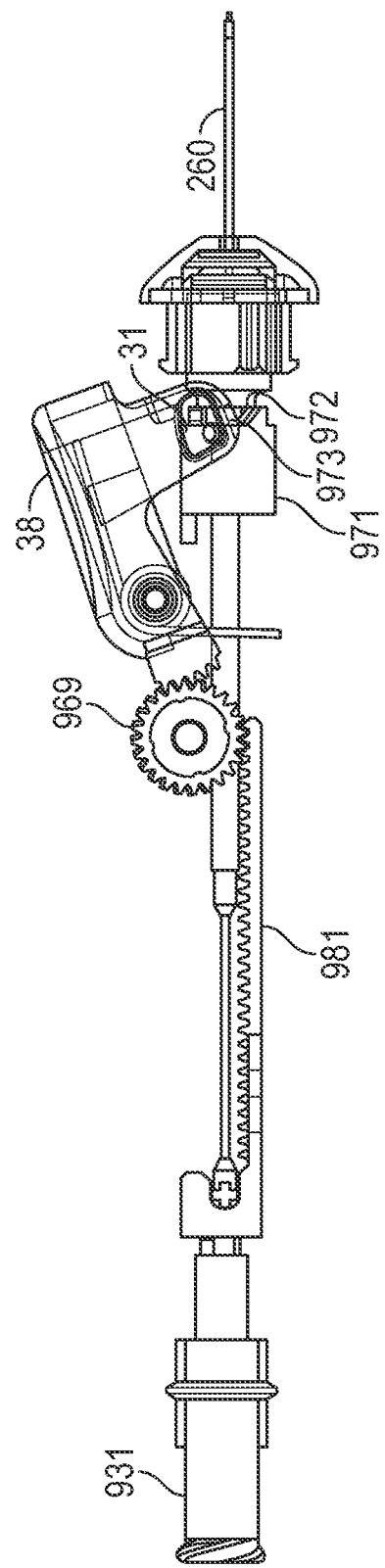

As shown in FIG. 13F, a one-way clutch 990 may provide for the drive gear teeth 977 of the drive gear 979 to engage the rack portion teeth 983 of the rack portion 981 in a ratchet and/or index process. For example, after the drive gear 979 rotates in the drive rotational direction 955 to move the rack portion the stroke length 970, the one-way clutch 990 allows the trigger gear 969 to rotate in the opposite direction without causing the drive gear 979 or drive axle 923 to rotate further in any direction, thus keeping the rack portion 981 in position while the button 38 resets (e.g., when the button 38 moves back to the un-pressed position shown in FIG. 13D). Thus, the one-way clutch 990 allows the drive gear 979 to rotate in the drive rotational direction 955 only so that the drive gear 979, and also the rack portion 981, stay in the same position when the button 38 is reset. The button 38 can be moved back to the un-pressed position when the user force 850 is removed (e.g., the user stops pressing down on the button 38) via a spring 984 (e.g., torsion spring), where a biasing force 960 pushes the button 38 back to the initial un-pressed or reset position. Once the button 38 is reset, the button 38 may be pressed again to start the process over again.

Each trigger of the button 38 may cause the button 38 to swing a distance (e.g., 20 degrees) and may cause the rack portion 981 to move forward a set number of rack portion teeth 983 (e.g., two teeth). Thus, the movement of the rack portion 981 may be a stroke length 970 of one tenth of the rack portion 981 containing the rack portion teeth 983, thereby limiting the use of the ophthalmic device 210 to ten activations (e.g., ten pumps). For example, as shown in FIG. 13C, the rear seal 999 on the rear end of the plunger 911 (e.g., the end closest to the inlet port 931) may be configured to pop free after a set number of activations (e.g., three activations). This can prevent additional substance added through the inlet port 931 from being retained in a bore tube 913 (e.g., the substance reservoir) of the ophthalmic device 210. Further, the front end of the plunger 911 (e.g., the end closest to the tip segment 151) may include a one-way valve 915 (e.g., a duck valve), a valve retainer 917 and a front seal 919 (e.g., O-ring seal). The one-way valve 915 can provide for priming the ophthalmic device 210 while preventing backflow of the substance during priming and pumping processes. Thus, the one-way valve 915 can seal the plunger 911 and provide for further activations (e.g., seven or more) after the rear seal 999 pops off following the first three activations, providing for a maximum number of activations that can be used by the ophthalmic device 210. Accordingly, the ophthalmic device 210 may be rendered unusable after ten activations (e.g., pump actions) for health and safety reasons, as well as to optimize the integrity of the device by minimizing wear of the components. For example, configuring the ophthalmic device 210 to be disposable after a set number of uses eliminates the need to clean/sterilize the device and avoids the issue of any of the seals 919, 999 drying up and failing.

Figure 14A:
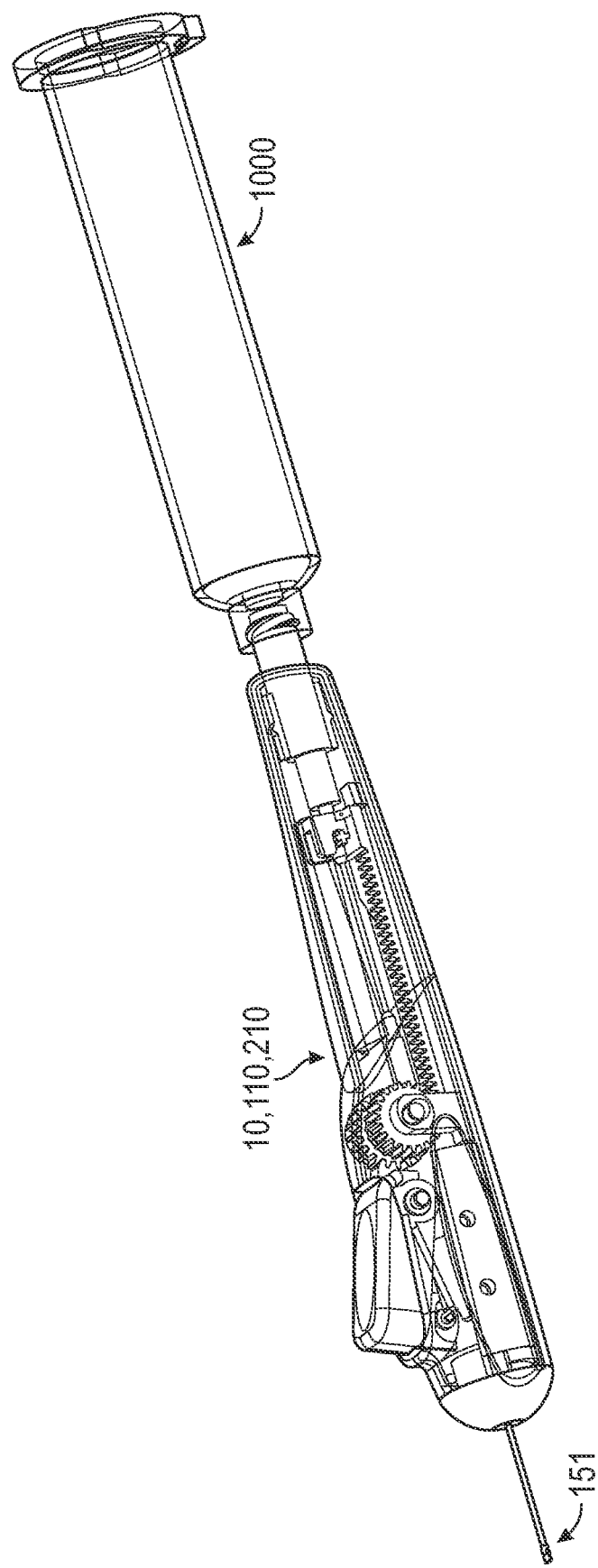
FIG. 14A is a perspective view of an example of an ophthalmic device and priming syringe assembly.
Figure 14B:
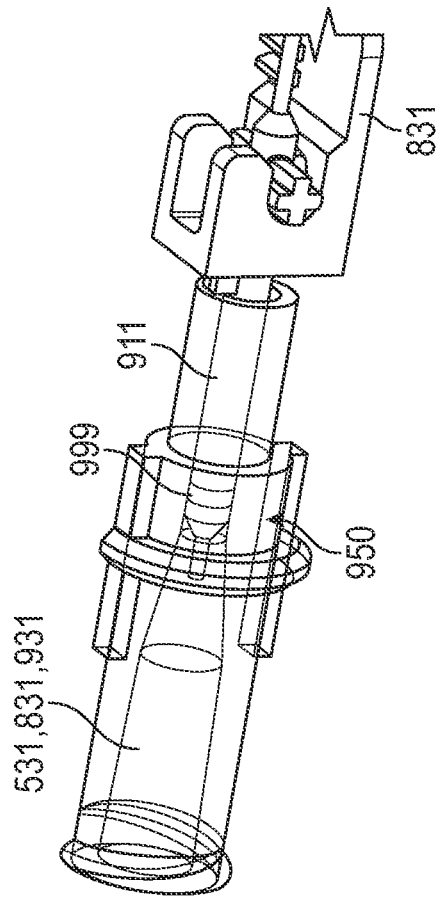
FIGS. 14B-14C are portion views of internal components of FIG. 14A, illustrating component action during priming.
Figure 14C:
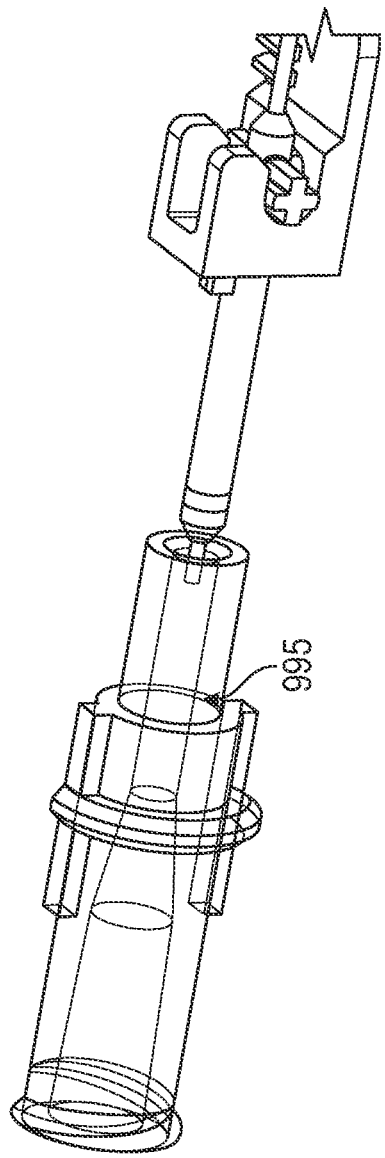

FIGS. 14A-14C illustrate the priming process for an ophthalmic device 10, 110, 210 in order to load the appropriate volume of substance (e.g., viscoelastic fluid) and to clear the fluid path of the ophthalmic device 10, 110, 210 of air. As shown in FIG. 14A, a syringe 1000 (e.g., standard luer port syringe) containing the desired substance can be coupled to the inlet port 531, 831, 931 and the substance can then be pushed throughout the fluid path of the ophthalmic device 10, 110, 210 until the substance comes out of the tip segment 151. The one-way valve 915 allows the substance to flow through towards the tip segment 151 while preventing any backflow of the substance back through the one-way valve 915. Once primed, the cannula 14 and the bore tube 913 can be full of the desired volume of the substance, such as enough volume for ten pumping actions, for example.

As shown in FIG. 14B, the rear end of the plunger 911 is sealingly engaged within the inlet port 531, 831, 931 via the rear seal 999. The rear end of the plunger 911 is shown in the starting position 950 (e.g., before or after priming, but before any activations) in FIG. 14B. During each activation (e.g., pumping action) of the ophthalmic device 10, 110, 210, the plunger 911 advances away from the inlet port 531, 831, 931 as the plunger 911 is moved forward the stroke length 970 for each pumping cycle. After a set number of activations (e.g., three activations), the rear end of the plunger 911 has advanced forward enough to separate or disengage from a cylinder 995 of the ophthalmic device 10, 110, 210, as shown in FIG. 14C. For example, the rear seal 999 can pop off from a sealing engagement with the interior of the cylinder 995, thus preventing the ophthalmic device 10, 110, 210 from being able to be re-primed. At this point, the substance flow path can contain just enough substance for the remainder of the desired activations (e.g., seven pumping actions). Accordingly, the ophthalmic device 10, 110, 210 cannot be re-primed, refilled or used for more than the total number of allowable pumping cycles (e.g., ten total pumping cycles).

Figure 15A:
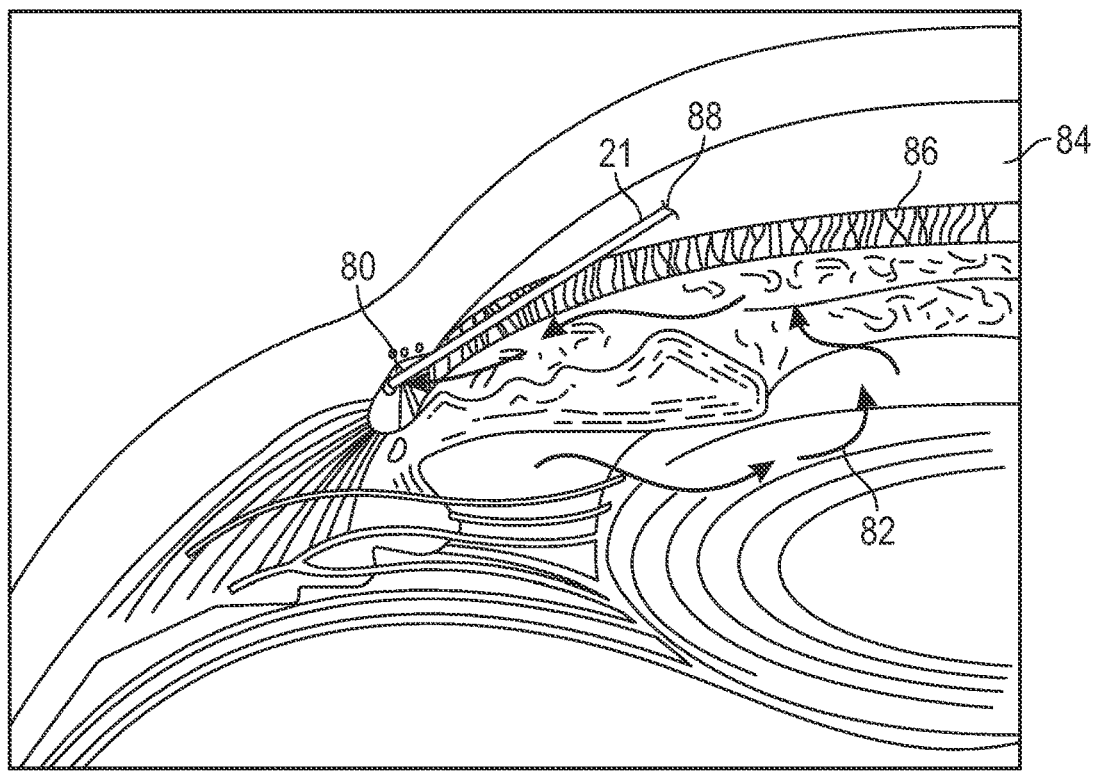
FIGS. 15A-15B are cutaway views showing an example of an ophthalmic procedure that can be performed with an ophthalmic device.
Figure 15B:
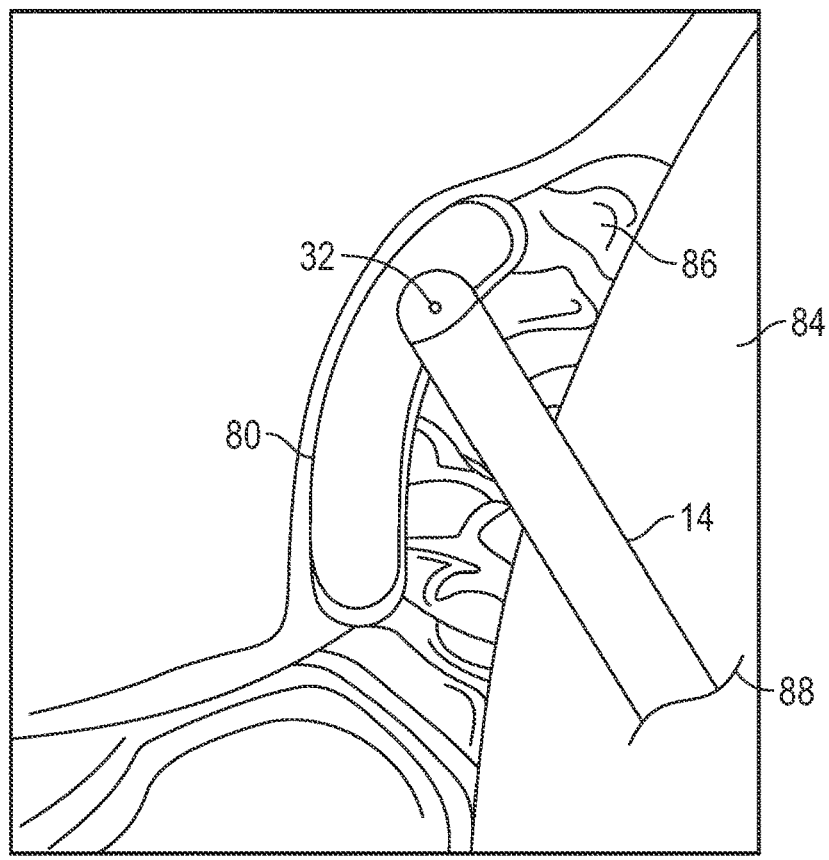

FIGS. 15A and 15B illustrate an exemplary method of performing an ophthalmic procedure using the ophthalmic device 10. The method can be used to deliver a substance (e.g., a fluid or gas) into, e.g., Schlemm's canal 80 or any other suitable portion of a patient's eye.

As noted above, in a healthy eye, a stream of aqueous humor 82 drains out of the anterior chamber 84 of the eye, through the trabecular meshwork 86 and then into Schlemm's canal 80 and distal collector channels. The aqueous humor 82 then exits through Schlemm's canal 80 into the collector channels and distal venous system. When this flow path of aqueous humor 82 is interrupted (e.g., due to diseased or damaged tissue in the trabecular meshwork 86 and/or Schlemm's canal 80), the IOP of an eye may rise, potentially resulting in a variety of medical concerns (e.g., glaucoma, loss of vision, optic nerve damage, etc.).

In order to improve the flow path of aqueous humor 82, a medical professional may insert ocular component 21 through an incision 88 made in the anterior chamber 84 and advance the distal end of sleeve 260 of the ocular component 21 to the trabecular meshwork 86 so that it abuts against or contacts the trabecular meshwork 86. The sleeve 260 (not visible in FIG. 15B) can then be retracted so that distal end of the cannula 14 including orifice(s) 32 enter the Schlemm's canal 80, as shown in FIG. 15B and as further described above using any of the mechanisms or components described herein.

With reference to FIG. 15B, once distal end of cannula 14 is inserted into Schlemm's canal 80 such that each of the one or more orifices 32 is fully housed within Schlemm's canal 80, the medical professional may inject a pre-defined dose or amount of fluid or other substance via actuation as discussed above. After injection of a pre-defined dose or amount of fluid or other substance through orifices 32, this process may be repeated any appropriate number of times, with the cannula 14 held in the same position and/or with the cannula 14 moved to one or more different positions to inject fluid in different locations and/or from different angles. Optionally, after the injection of one or more pre-defined doses of fluid or other substance at a certain location within Schlemm's canal 80, distal end of the cannula 14 may be retracted and repositioned within the eye. In some arrangements, such repositioning may occur via withdrawal of cannula 14 from incision 88 (e.g., a first incision), and reinsertion through an additional incision, spaced from the first incision. Additionally or alternatively, such repositioning may include retraction of distal end 30 from Schlemm's canal 80 and/or trabecular meshwork 86 and then relocation into a new portion of Schlemm's canal 80 without removal of cannula 14 from the first incision 88. In some implementations, fluid may be delivered into the Schlemm's canal 80 and trabecular meshwork 86 simultaneously, causing the Schlemm's canal 80 to open and deliver the fluid into the various layers of the trabecular meshwork 86.

It is to be understood that while the foregoing description describes devices and methods for injection of a fluid or other substance through orifices 32, the ophthalmic device 10 described herein may be arranged for precision-controlled aspiration of fluid or other substances away from the eye. For example, ophthalmic device 10 may be actuated in a reverse manner from that described above to achieve a removal of fluid or other substances from the eye.

One or more embodiments of the subject technology may include an ophthalmic device comprising: a cannula having a cannula distal end, a lumen, and one or more orifices coupled to the lumen, the cannula configured to deliver a fluid; a sleeve disposed around the cannula and having a sleeve distal end; a handle coupled to the sleeve and the cannula at a handle distal end, the handle having an actuator; and an internal mechanism coupled to the actuator and configured to pump the fluid, the internal mechanism comprising: an inlet port disposed on a handle proximal end; a drive member coupled to the actuator, the drive member comprising a plurality of drive teeth; and a plunger coupled to the drive member, the plunger comprising a plurality of plunger teeth, wherein rotation of the drive member is configured to provide a force that moves the plunger in a distal direction along a longitudinal axis of the handle when the actuator moves from an un-pressed position to a pressed position, the movement of the plunger causing the fluid to move distally through the handle and the cannula, and a portion of the fluid to exit the one or more orifices.

One or more embodiments of the subject technology may include an internal mechanism for an ophthalmic device, the internal mechanism comprising: an inlet port; a drive member comprising a plurality of drive teeth; a plunger having a first portion comprising a plurality of plunger teeth, the first portion engaged with the drive member; and a trigger member coupled to the drive member via a coupling, the trigger member configured to engage with an actuator, wherein the trigger member is configured to rotate in a first rotational direction from an activation movement of the actuator, wherein the drive member is configured to rotate in the first rotational direction via the coupling and to provide a force on the first portion of the plunger that moves the plunger in a first linear direction, wherein the movement of the plunger in the first linear direction is configured to cause a fluid to pump through the ophthalmic device.

While principles of the present disclosure are described herein with reference to illustrative embodiments for particular applications, it should be understood that the disclosure is not limited thereto. Those having ordinary skill in the art and access to the teachings provided herein will recognize additional modifications, applications, embodiments, and substitution of equivalents all fall within the scope of the embodiments described herein. Accordingly, the invention is not to be considered as limited by the foregoing description.

A reference to an element in the singular is not intended to mean one and only one unless specifically so stated, but rather one or more. For example, "a" module may refer to one or more modules. An element proceeded by "a," "an," "the," or "said" does not, without further constraints, preclude the existence of additional same elements.

Headings and subheadings, if any, are used for convenience only and do not limit the invention. The word exemplary is used to mean serving as an example or illustration. To the extent that the term include, have, or the like is used, such term is intended to be inclusive in a manner similar to the term comprise as comprise is interpreted when employed as a transitional word in a claim. Relational terms such as first and second and the like may be used to distinguish one entity or action from another without necessarily requiring or implying any actual such relationship or order between such entities or actions.

Phrases such as an aspect, the aspect, another aspect, some aspects, one or more aspects, an implementation, the implementation, another implementation, some implementations, one or more implementations, an embodiment, the embodiment, another embodiment, some embodiments, one or more embodiments, a configuration, the configuration, another configuration, some configurations, one or more configurations, the subject technology, the disclosure, the present disclosure, other variations thereof and alike are for convenience and do not imply that a disclosure relating to such phrase(s) is essential to the subject technology or that such disclosure applies to all configurations of the subject technology. A disclosure relating to such phrase(s) may apply to all configurations, or one or more configurations. A disclosure relating to such phrase(s) may provide one or more examples. A phrase such as an aspect or some aspects may refer to one or more aspects and vice versa, and this applies similarly to other foregoing phrases.

A phrase "at least one of" preceding a series of items, with the terms "and" or "or" to separate any of the items, modifies the list as a whole, rather than each member of the list. The phrase "at least one of" does not require selection of at least one item; rather, the phrase allows a meaning that includes at least one of any one of the items, and/or at least one of any combination of the items, and/or at least one of each of the items. By way of example, each of the phrases "at least one of A, B, and C" or "at least one of A, B, or C" refers to only A, only B, or only C; any combination of A, B, and C; and/or at least one of each of A, B, and C.

It is understood that the specific order or hierarchy of steps, operations, or processes disclosed is an illustration of exemplary approaches. Unless explicitly stated otherwise, it is understood that the specific order or hierarchy of steps, operations, or processes may be performed in different order. Some of the steps, operations, or processes may be performed simultaneously. The accompanying method claims, if any, present elements of the various steps, operations or processes in a sample order, and are not meant to be limited to the specific order or hierarchy presented. These may be performed in serial, linearly, in parallel or in different order. It should be understood that the described instructions, operations, and systems can generally be integrated together in a single software/hardware product or packaged into multiple software/hardware products.

In one aspect, a term coupled or the like may refer to being directly coupled. In another aspect, a term coupled or the like may refer to being indirectly coupled.

Terms such as top, bottom, front, rear, side, horizontal, vertical, and the like refer to an arbitrary frame of reference, rather than to the ordinary gravitational frame of reference.

Thus, such a term may extend upwardly, downwardly, diagonally, or horizontally in a gravitational frame of reference.

The disclosure is provided to enable any person skilled in the art to practice the various aspects described herein. In some instances, well-known structures and components are shown in block diagram form in order to avoid obscuring the concepts of the subject technology. The disclosure provides various examples of the subject technology, and the subject technology is not limited to these examples. Various modifications to these aspects will be readily apparent to those skilled in the art, and the principles described herein may be applied to other aspects.

All structural and functional equivalents to the elements of the various aspects described throughout the disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112(f), unless the element is expressly recited using the phrase "means for" or, in the case of a method claim, the element is recited using the phrase "step for".

The title, background, brief description of the drawings, abstract, and drawings re hereby incorporated into the disclosure and are provided as illustrative examples of the disclosure, not as restrictive descriptions. It is submitted with the understanding that they will not be used to limit the scope or meaning of the claims. In addition, in the detailed description, it can be seen that the description provides illustrative examples and the various features are grouped together in various implementations for the purpose of streamlining the disclosure. The method of disclosure is not to be interpreted as reflecting an intention that the claimed subject matter requires more features than are expressly recited in each claim. Rather, as the claims reflect, inventive subject matter lies in less than all features of a single disclosed configuration or operation. The claims are hereby incorporated into the detailed description, with each claim standing on its own as a separately claimed subject matter.

The claims are not intended to be limited to the aspects described herein, but are to be accorded the full scope consistent with the language of the claims and to encompass all legal equivalents. Notwithstanding, none of the claims are intended to embrace subject matter that fails to satisfy the requirements of the applicable patent law, nor should they be interpreted in such a way.

What is claimed is:

1. An ophthalmic device comprising:
a cannula having a cannula distal end, a lumen, and one or more orifices coupled to the lumen, the cannula configured to deliver a fluid;
a sleeve disposed around the cannula and having a sleeve distal end;
a handle coupled to the sleeve and the cannula at a handle distal end, the handle having an actuator; and
an internal mechanism coupled to the actuator and configured to pump the fluid, the internal mechanism comprising:
an inlet port disposed on a handle proximal end;
a drive member coupled to the actuator; and
a plunger coupled to the drive member, wherein rotation of the drive member is configured to provide a force that moves the plunger in a distal direction along a longitudinal axis of the handle when the actuator moves from an un-pressed position to a pressed position, the movement of the plunger causing the fluid to move distally through the handle and the cannula, and a portion of the fluid to exit the one or more orifices,
wherein the ophthalmic device is configured to retain a volume of fluid and to be prevented from being re-primed after a predetermined number of actuator presses, wherein the retained volume of fluid is dispensed over an additional number of actuator pushes.

2. The ophthalmic device of claim 1, wherein:
the actuator includes a push button positioned on the handle and is moveable from the un-pressed position to the pressed position upon application of a user force; and
upon movement of the push button from the un-pressed position to the pressed position, the push button is configured to urge rotation of the drive member in a drive rotational direction.

3. The ophthalmic device of claim 1, further comprising:
a reset spring coupled to the actuator, the reset spring configured to urge the actuator from the pressed position back to the un-pressed position.

4. The ophthalmic device of claim 1, the internal mechanism further comprising:
a plunger tube coupled to a distal end of the plunger; and
a seal coupled to a distal end of the plunger tube, the seal configured to prevent backflow of the fluid in a proximal direction.

5. The ophthalmic device of claim 1, wherein:
the drive member comprises a plurality of drive teeth;
the drive member is engaged with a first portion of the plunger comprising a plurality of plunger teeth; and
rotation of the drive member causes the plunger to advance in the distal direction.

6. The ophthalmic device of claim 1, the internal mechanism further comprising a trigger gear coupled to the drive member via a drive axle, wherein:
the trigger gear comprises a plurality of trigger teeth;
the actuator comprises a plurality of actuator teeth; and
movement of the actuator to the pressed position comprises rotation of the actuator about an actuator axle, causing the actuator teeth to move along the trigger teeth and move the trigger gear in a drive rotational direction, the movement of the trigger gear causing the drive member to also move in the drive rotational direction via the drive axle.

7. The ophthalmic device of claim 6, the internal mechanism further comprising a one-way clutch coupled to the trigger gear and configured to provide engagement of the trigger gear with the drive axle in an indexing configuration, wherein during movement of the actuator back to the un-pressed position, the one-way clutch is configured to disengage the trigger gear from the drive axle to allow the trigger gear to rotate in a direction opposite to the drive rotational direction without further movement of the drive axle and the drive member.

8. The ophthalmic device of claim 1, wherein:
the sleeve is operationally coupled to the actuator; and
the rotation of the actuator about an actuator axle causes the sleeve to retract from the cannula distal end so that the fluid is delivered to the cannula distal end while the sleeve is in a retracted proximal position.

9. The ophthalmic device of claim 1, the internal mechanism further comprising:
a bore tube coupled to a distal end of the plunger; and a front seal coupled to a distal end of the plunger, the front seal configured to prevent backflow of the fluid in a proximal direction through the bore tube.

10. The ophthalmic device of claim 1, the internal mechanism further comprising a one-way valve coupled to a distal end of the plunger, the one-way valve configured to allow fluid flow in the distal direction during priming actions, and to prevent backflow of the fluid past the distal end of the plunger in the proximal direction.

11. The ophthalmic device of claim 1, the internal mechanism further comprising a rear seal coupled to a proximal end of the plunger, the rear seal configured to prevent fluid from leaking out of the plunger when the device is being primed.

12. The ophthalmic device of claim 11, the internal mechanism further comprising a cylinder coupled to the inlet port, the cylinder configured to slidingly receive the proximal end of the plunger.

13. The ophthalmic device of claim 12, wherein
the proximal end of the plunger is configured to slide within the cylinder in the distal direction during each press of the actuator.

14. The ophthalmic device of claim 13, wherein the rear seal is configured to disengage from a sealing engagement with the cylinder after the predetermined number of actuator presses to prevent the ophthalmic device from being able to be re-primed.

15. The ophthalmic device of claim 1, further comprising a rear seal disposed within the inlet port, the rear seal configured to disengage from the inlet port after the predetermined number of actuator presses of the ophthalmic device, preventing additional fluid added through the inlet port from being moved through the cannula to the one or more orifices.

16. The ophthalmic device of claim 15, the internal mechanism further comprising a one-way valve coupled to the plunger, the one-way valve configured to allow fluid flow in the distal direction during priming actions, to prevent backflow of the fluid past the distal end of the plunger in the proximal direction, and to seal the plunger and provide for further activations of the ophthalmic device after the rear seal is disengaged from the inlet port.

* * * * *